(12) United States Patent
Sklar

(10) Patent No.: US 12,409,090 B2
(45) Date of Patent: Sep. 9, 2025

(54) SURGICAL UNIVERSAL HEADREST INCLUDING SKULL PIN HOLDER ASSEMBLY

(71) Applicant: Frederick H. Sklar, Dallas, TX (US)

(72) Inventor: Frederick H. Sklar, Dallas, TX (US)

( * ) Notice: Subject to any disclaimer, the term of this patent is extended or adjusted under 35 U.S.C. 154(b) by 0 days.

(21) Appl. No.: 18/502,807

(22) Filed: Nov. 6, 2023

(65) Prior Publication Data

US 2024/0148583 A1    May 9, 2024

Related U.S. Application Data

(60) Provisional application No. 63/382,711, filed on Nov. 7, 2022.

(51) Int. Cl.
| | | |
|---|---|---|
| A61G 13/12 | (2006.01) | |
| A61B 90/14 | (2016.01) | |
| A61B 46/20 | (2016.01) | |

(52) U.S. Cl.
CPC ............ *A61G 13/121* (2013.01); *A61B 90/14* (2016.02); *A61G 13/129* (2013.01); *A61B 46/20* (2016.02); *A61G 2200/14* (2013.01); *A61G 2200/325* (2013.01)

(58) Field of Classification Search
CPC ....... A61B 90/14; A61B 5/1126; A61B 5/746; A61B 90/36; A61B 2090/365; A61B 2018/00791; A61B 2018/00988; A61B 2090/0803; A61B 2090/0804; A61B 2090/0809; A61B 2090/0814; A61B 90/10; A61B 2034/2068; A61B 34/20;

(Continued)

(56) References Cited

U.S. PATENT DOCUMENTS

| | | |
|---|---|---|
| 2,494,792 A | 1/1950 | Bloom |
| 2,966,383 A | 12/1960 | Boetcker et al. |
| 3,072,118 A | 1/1963 | Standerwick et al. |

(Continued)

FOREIGN PATENT DOCUMENTS

| | | |
|---|---|---|
| EP | 2316521 | 5/2011 |
| JP | S55-052747 | 4/1980 |

(Continued)

OTHER PUBLICATIONS

International Search Report and Written Opinion dated Mar. 1, 2011 regarding Intl. Patent Application No. PCT/US2011/020906; 9 pgs.

(Continued)

*Primary Examiner* — Ophelia A Hawthorne
(74) *Attorney, Agent, or Firm* — Scott Griggs; Griggs Bergen LLP

(57) ABSTRACT

A surgical universal headrest is disclosed. In one embodiment, a body has two lateral wings slidably coupled to the body. Each lateral wing has an arm moveably secured thereto with a range of proximal-to-distal motion with respect to a medial line of the body. The body, lateral wings, and the arms, in cooperative combination, define a support perimeter of adjustable size having an opening therethrough. The support perimeter of adjustable size accommodates patients ranging from premature infants to adults and the opening accommodates an eye-nose-mouth region of a patient ranging from a premature infant to an adult. A skull pin holder assembly is included.

10 Claims, 18 Drawing Sheets

(58) Field of Classification Search
CPC .... A61B 46/20; A61G 13/121; A61G 13/129; A61G 2200/14; A61G 2200/325
See application file for complete search history.

(56) References Cited

U.S. PATENT DOCUMENTS

| | | |
|---|---|---|
| 3,099,441 A | 7/1963 | Ries |
| 3,522,799 A | 8/1970 | Gauthier |
| 3,604,412 A | 9/1971 | Gardner |
| 3,810,462 A | 5/1974 | Szpur |
| 3,835,861 A | 9/1974 | Kees, Jr. et al. |
| 3,923,046 A | 12/1975 | Heifetz |
| 3,958,558 A | 5/1976 | Dunphy et al. |
| 4,014,319 A | 3/1977 | Favre |
| 4,108,426 A | 8/1978 | Lindstroem et al. |
| 4,143,652 A | 3/1979 | Meier et al. |
| 4,169,478 A | 10/1979 | Hickmann |
| 4,254,763 A | 3/1981 | Cready et al. |
| 4,281,667 A | 8/1981 | Cosman |
| 4,333,638 A | 6/1982 | Gillotti |
| 4,360,028 A | 11/1982 | Moran et al. |
| 4,444,179 A | 4/1984 | Trippi |
| 4,457,300 A | 7/1984 | Budde |
| 4,465,069 A | 8/1984 | Moran et al. |
| 4,545,572 A | 10/1985 | Day |
| 4,667,660 A | 5/1987 | Eingorn |
| 4,681,559 A | 7/1987 | Hooven |
| 4,700,691 A | 10/1987 | Tari et al. |
| 4,995,401 A | 2/1991 | Bunegin et al. |
| 5,135,283 A | 8/1992 | Cassese et al. |
| 5,147,287 A | 9/1992 | Jewell et al. |
| 5,197,965 A | 3/1993 | Cherry et al. |
| 5,205,815 A | 4/1993 | Saunders |
| 5,214,815 A | 6/1993 | Agbodoe et al. |
| 5,254,079 A | 10/1993 | Agbodoe et al. |
| 5,269,034 A | 12/1993 | Day et al. |
| 5,276,927 A | 1/1994 | Day |
| 5,284,129 A | 2/1994 | Agbodoe et al. |
| 5,317,771 A | 6/1994 | Cook |
| 5,318,509 A | 6/1994 | Agbodoe |
| 5,326,374 A | 7/1994 | Ilbawi et al. |
| 5,347,894 A | 9/1994 | Fischer |
| 5,529,358 A | 6/1996 | Dinkler et al. |
| 5,537,704 A | 7/1996 | Dinkler |
| 5,564,663 A | 10/1996 | Cook et al. |
| 5,674,186 A | 10/1997 | Guigui et al. |
| 5,806,512 A | 9/1998 | Abramov et al. |
| 5,832,926 A | 11/1998 | Towlen |
| 6,117,143 A | 9/2000 | Hynes et al. |
| 6,179,846 B1 | 1/2001 | McFadden |
| 6,283,934 B1 | 9/2001 | Borgesen |
| 6,306,085 B1 | 10/2001 | Farascioni |
| 6,306,146 B1 | 10/2001 | Dinkler |
| 6,315,783 B1 | 11/2001 | Katz et al. |
| 6,368,330 B1 | 4/2002 | Hynes et al. |
| 6,381,783 B2 | 5/2002 | Reinhardt et al. |
| 6,416,468 B2 | 7/2002 | Deckman et al. |
| 6,463,765 B2 | 10/2002 | Blakely |
| 6,557,195 B2 | 5/2003 | Dinkler |
| 6,584,630 B1 | 7/2003 | Dinkler |
| 6,594,839 B1 | 7/2003 | Papay |
| 6,602,190 B2 | 8/2003 | Dobrovolny |
| 6,629,982 B2 | 10/2003 | Day et al. |
| 6,684,428 B2 | 2/2004 | Grotehuis et al. |
| 6,770,082 B2 | 8/2004 | Dominguez et al. |
| 7,024,892 B2 | 4/2006 | Blakely |
| 7,117,551 B1 | 10/2006 | Dinkler, II et al. |
| 7,229,451 B2 | 6/2007 | Day et al. |
| 7,232,411 B2 | 6/2007 | Dinkler, II et al. |
| 7,326,177 B2 | 2/2008 | Williamson, IV et al. |
| 7,507,244 B2 | 3/2009 | Dinkler |
| 7,510,533 B2 | 3/2009 | Mauge et al. |
| 7,552,492 B2 * | 6/2009 | Rolfes .................... A61B 90/14 5/643 |
| 7,730,563 B1 | 6/2010 | Sklar et al. |
| 7,882,574 B2 | 2/2011 | Arsenault |
| 7,945,970 B2 | 5/2011 | Belluye et al. |
| 7,949,394 B2 | 5/2011 | Salo et al. |
| 8,037,884 B2 | 10/2011 | Weinstein et al. |
| 8,105,256 B1 | 1/2012 | Ariza |
| 8,257,289 B2 | 9/2012 | Vess |
| 8,292,856 B2 | 10/2012 | Bertrand et al. |
| 8,568,195 B1 | 10/2013 | Schindler |
| 8,646,452 B2 | 2/2014 | Sklar |
| 8,801,711 B2 | 8/2014 | Solomon et al. |
| 9,033,909 B2 | 5/2015 | Aihara |
| 9,211,224 B2 | 12/2015 | Sklar |
| 9,216,125 B2 | 12/2015 | Sklar |
| 9,717,890 B2 | 8/2017 | Holper et al. |
| 9,925,360 B2 | 3/2018 | Ludin et al. |
| 10,743,954 B2 | 8/2020 | Sklar |
| 11,103,683 B1 | 8/2021 | Sklar |
| 11,154,695 B2 | 10/2021 | Sklar |
| 11,324,933 B2 | 5/2022 | Sklar |
| 11,389,630 B2 | 7/2022 | Sklar |
| 11,471,231 B2 | 10/2022 | Sklar et al. |
| 11,678,947 B2 | 6/2023 | Sklar |
| 2001/0029379 A1 * | 10/2001 | Grotehuis ............... A61B 90/14 606/130 |
| 2002/0042619 A1 | 4/2002 | Dominguez et al. |
| 2002/0151907 A1 | 10/2002 | Day et al. |
| 2004/0097985 A1 | 5/2004 | Day et al. |
| 2005/0075650 A1 | 4/2005 | Dinkler |
| 2005/0277832 A1 | 12/2005 | Foley et al. |
| 2008/0139959 A1 | 6/2008 | Miethke et al. |
| 2008/0269777 A1 | 10/2008 | Appenrodt et al. |
| 2009/0138064 A1 | 5/2009 | Horn |
| 2009/0192432 A1 | 7/2009 | Frazer |
| 2009/0204019 A1 | 8/2009 | Ginggen et al. |
| 2009/0254017 A1 | 10/2009 | Dumpson et al. |
| 2009/0287084 A1 | 11/2009 | Ragauskas et al. |
| 2009/0299258 A1 | 12/2009 | Cureington-Sims |
| 2011/0054373 A1 | 3/2011 | Reiley |
| 2011/0066072 A1 | 3/2011 | Kawoos et al. |
| 2011/0168184 A1 | 7/2011 | Sklar |
| 2012/0226215 A1 | 9/2012 | Hsu et al. |
| 2013/0085400 A1 | 4/2013 | Oliveira et al. |
| 2013/0095730 A1 | 4/2013 | Jensen |
| 2013/0096557 A1 * | 4/2013 | Dinkler, II ......... A61B 17/6433 606/59 |
| 2014/0378774 A1 | 12/2014 | Wooster |
| 2015/0005800 A1 | 1/2015 | Anite |
| 2015/0268673 A1 | 9/2015 | Farzbod et al. |
| 2019/0009014 A1 | 1/2019 | Chen et al. |
| 2020/0061355 A1 | 2/2020 | Barnea et al. |
| 2022/0110701 A1 * | 4/2022 | Crawford ............... A61B 34/76 |
| 2022/0257913 A1 | 8/2022 | Sklar |
| 2022/0387126 A1 * | 12/2022 | Moosmann ............ A61B 90/10 |

FOREIGN PATENT DOCUMENTS

| | | |
|---|---|---|
| JP | H09-075369 | 3/1997 |
| JP | H09-147142 | 6/1997 |
| WO | 2018227022 | 12/2018 |
| WO | 2019241753 | 12/2019 |

OTHER PUBLICATIONS

International Search Report and Written Opinion dated Oct. 18, 2012 regarding Intl. Patent Application No. PCT/US12/47894; 11 pgs.

International Search Report and Written Opinion dated May 6, 2013 regarding Intl. Patent Application No. PCT/US13/26207; 16 pgs.

International Search Report and Written Opinion dated Jun. 30, 2021 regarding Intl. Patent Application No. PCT/US21/17365; 12 pgs.

Turnbull et al.; "Post-dural puncture headache: pathogenesis, prevention and treatment"; British Journal of Anaesthesia; 2003; 91(5); pp. 718-729.

International Search Report and Written Opinion dated Aug. 31, 2018 regarding Intl. Patent Application No. PCT/US18/36558; 12 pgs.

(56) References Cited

OTHER PUBLICATIONS

Farlex Partner Medical Dictionary. S.v. "costal marin." Retrieved Jan. 11, 2016 from http://medical-dictionary.thefreedictionary.com/costal+margin; 1 pg.
Sklar et al.; "The Use of Abdominal Binders to Treat Over-Shunting Headaches"; J. Neurosurg. Pediatr.; Jun. 2012; 9(6); pp. 615-620; doI: 10.3171/2012.2.PEDS11146; Children's Medical Center, Dallas, Texas, USA.

* cited by examiner

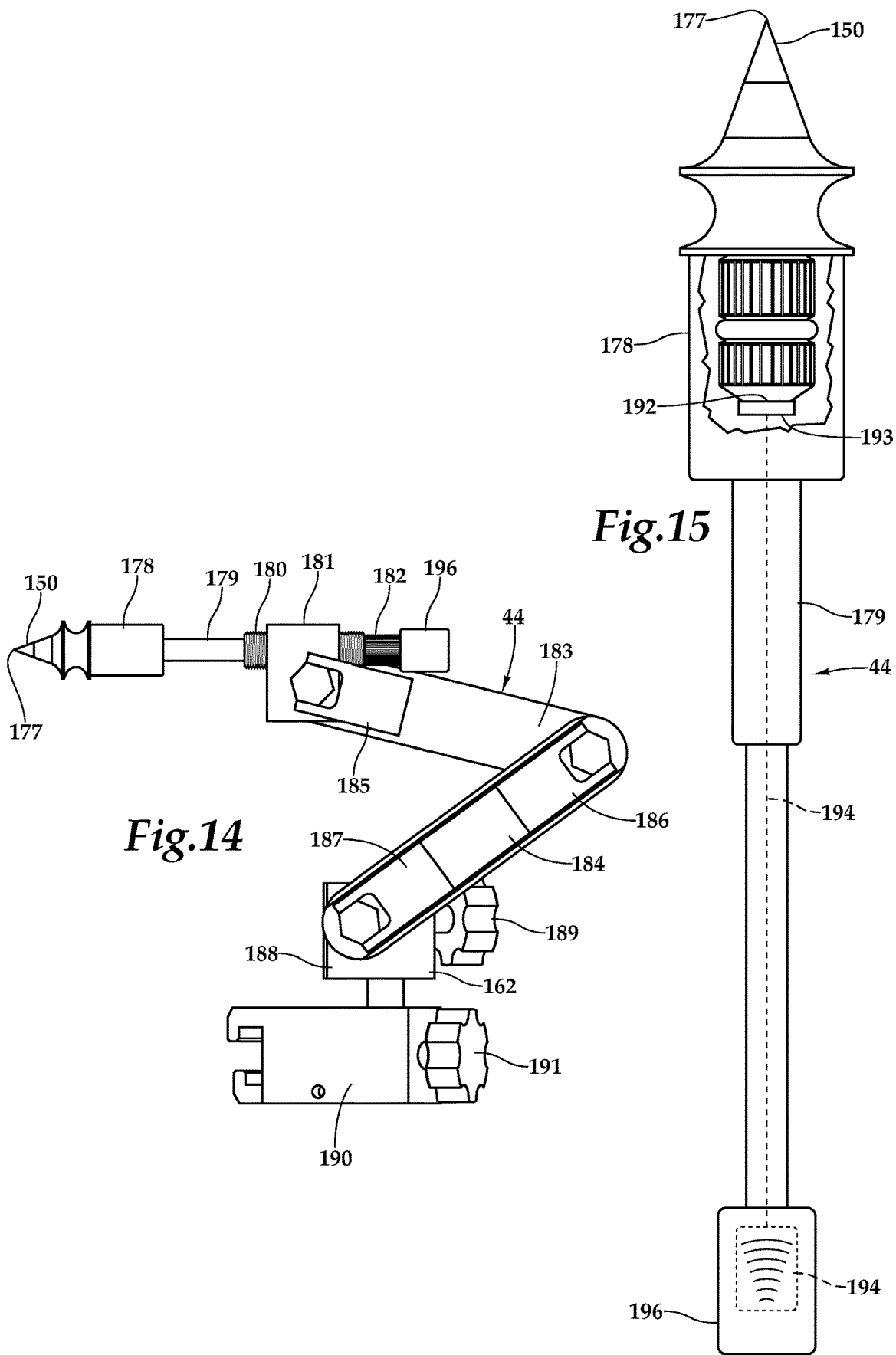

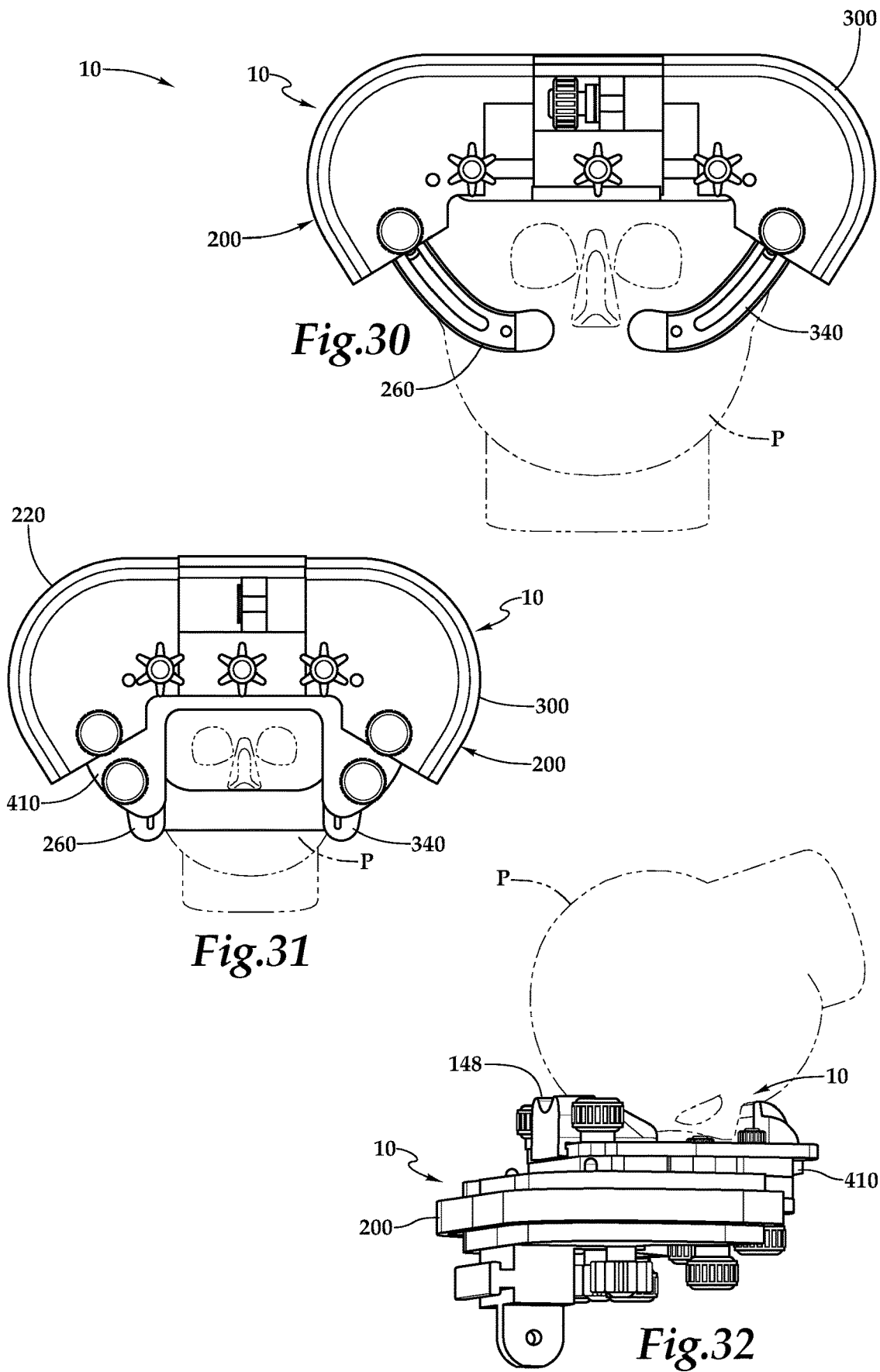

SURGICAL UNIVERSAL HEADREST INCLUDING SKULL PIN HOLDER ASSEMBLY

PRIORITY STATEMENT & CROSS-REFERENCE TO RELATED APPLICATIONS

This application claims priority from U.S. Patent Application No. 63/382,711, entitled "Surgical Universal Headrest" and filed on Nov. 7, 2022, in the name of Frederick H. Sklar; which is hereby incorporated by reference for all purposes.

This application discloses subject matter related to the subject matter disclosed in the following commonly owned, co-pending patent applications: U.S. patent application Ser. No. 18/502,795, entitled "Surgical Universal Headrest Including Skull Pin Holder Assembly" and filed on Nov. 6, 2023, in the name of Frederick H. Sklar; U.S. patent application Ser. No. 18/502,811, entitled "Surgical Universal Headrest Including Skull Pin Holder Assembly" and filed on Nov. 6, 2023, in the name of Frederick H. Sklar; U.S. patent application Ser. No. 18/502,815, entitled "Surgical Universal Headrest Including Skull Pin Holder Assembly" and filed on Nov. 6, 2023, in the name of Frederick H. Sklar; U.S. patent application Ser. No. 18/502,820, entitled "Base Station Assembly for an Operating Room Table" and filed on Nov. 6, 2023, in the name of Frederick H. Sklar; U.S. patent application Ser. No. 18/502,825, entitled "Base Station Assembly for an Operating Room Table" and filed on Nov. 6, 2023, in the name of Frederick H. Sklar; U.S. patent application Ser. No. 18/502,839, entitled "Base Station Assembly for an Operating Room Table" and filed on Nov. 6, 2023, in the name of Frederick H. Sklar; U.S. patent application Ser. No. 18/502,841, entitled "Surgical Armrest" and filed on Nov. 6, 2023, in the name of Frederick H. Sklar; all of which are hereby incorporated by reference, in entirety, for all purposes.

TECHNICAL FIELD OF THE INVENTION

This invention relates, in general, to surgical appliances and, in particular, to a surgical universal headrest used to support a patient's head, during a surgical procedure, such as an operative microsurgical procedure on a skull and brain.

BACKGROUND OF THE INVENTION

It is generally accepted that the head of an adult patient undergoing intracranial microneurosurgery must be supported in a neurosurgical headrest with pins—such as the many different neurosurgical headrests that are presently in use. In adults, skull clamps with pins not only support the head, but also provide the rigid fixation necessary for safe microsurgery and/or image guidance technology. In small children, however, their thin skulls and disproportionately large heads make it risky to use adult neurosurgical headrests with pins. It is dangerous to use high pressure pins in many patients under five years old. The pins can transiently deform the cranial bones, penetrate the skull, cause fractures, displace bone fragments into the brain, cause intracranial hemorrhage, and even allow the child to fall out of the headrest during surgery. These complications can evolve into a real catastrophic surgical event. The use of traditional pin fixation at pressures high enough to support the weight of a child's head is simply not safe or advisable in children with thin skulls and fibrous cranial sutures.

Accordingly, many pediatric neurosurgeons undertake microneurosurgical procedures on small children with the child's head supported only in a horseshoe headrest. But the head is free to move-dangerous during surgery under the microscope. Moreover, with a child in the prone position, the horseshoe headrest provides direct support of the forehead, but the lateral wings of the horseshoe function by squeezing the patient's cheeks (i.e., the midface). The face is wedged into the opening of the horseshoe much like a cork in the top of a bottle. The headrest is therefore in very close proximity to the lateral orbits. Any movement of the head within the horseshoe headrest during surgery can result in one side of the horseshoe pressing directly against an eye, possibly causing ocular damage. Furthermore, the use of image guidance is much less than ideal under these circumstances. Accordingly, there is a real need for a safe and dependable pediatric neurosurgical headrest that ensures cranial stabilization.

SUMMARY OF THE INVENTION

It would be advantageous to achieve a universal surgical headrest used to support a patient ranging from a premature infant to an adult, during a surgical procedure, such as an operative microsurgery procedure on a skull and brain. It would also be desirable to enable mechanical and medical-based solutions that would provide a safe and dependable neurosurgical headrest that ensures cranial stabilization that mitigates risks, such as ocular damage or high-pressure pin complications.

In one aspect, some embodiments are directed to a surgical universal headrest. In one embodiment, a body has two lateral wings slidably coupled to the body. Each lateral wing has an arm moveably secured thereto with a range of proximal-to-distal motion with respect to a medial line of the body. The body, lateral wings, and the arms, in cooperative combination, define a support perimeter of adjustable size having an opening therethrough. The support perimeter of adjustable size accommodates patients ranging from premature infants to adults and the opening accommodates an eye-nose-mouth region of a patient ranging from a premature infant to an adult.

In another aspect, some embodiments are directed to a surgical universal headrest with gel pads secured to a support perimeter to accommodate various patients and patient positions, such as a supine adult set up for a right pterional operative approach, a supine five (5)-month child set up for a bifrontal craniotomy, a twenty-eight (28)-week gestational age premature infant set up for a lateral surgical approach, prone positioning of a sixteen (16)-year old, prone positioning of a full term newborn, or prone positioning of a thirty-two (32)-week gestational age premature infant. The gel pads may include forehead gel pads, maxillary gel pads, round gel pads, and oval gel pads, for example. In still another aspect, some embodiments are directed to a surgical universal headrest utilizing a premature infant insert. The premature infant insert is secured to a support perimeter of adjustable size of the surgical universal headrest in a collapsed position. The premature infant insert reduces an opening to a size to accommodate an eye-nose-mouth region of a premature infant and provides appropriate gel pads for the premature infant. In a still further aspect, some embodiments are directed to a skull pin holder assembly including a pin, micro strain measuring device and transmitter. These and other aspects of the invention will be apparent from and elucidated with reference to the embodiments described hereinafter.

BRIEF DESCRIPTION OF THE DRAWINGS

For a more complete understanding of the features and advantages of the present invention, reference is now made to the detailed description of the invention along with the accompanying figures in which corresponding numerals in the different figures refer to corresponding parts and in which:

FIG. 14 is a sectional analysis of an embodiment of the pin assembly which utilizes a mechanical indicator of pin pressure;

FIG. 15 is a sectional analysis of an embodiment of the pin assembly which utilizes a micro strain measuring device;

FIG. 30 is a ventral plan view of one embodiment of the surgical universal headrest being utilized with prone positioning of a sixteen (16)-year old patient during a surgical procedure, such as an operative procedure on a skull and brain of the patient;

FIG. 31 is a ventral plan view of one embodiment of the surgical universal headrest being utilized with prone positioning of a full-term newborn patient during a surgical procedure, such as an operative procedure on a skull and brain of the full-term newborn patient;

FIG. 32 is a lateral perspective view of one embodiment of the surgical universal headrest with a premature insert being utilized for prone positioning of a thirty-two (32)-week gestational age baby patient during a surgical procedure, such as a posterior fossa operation on the skull and brain of the thirty-two (32)-week gestational age baby patient;

DETAILED DESCRIPTION OF THE INVENTION

Figure 1:
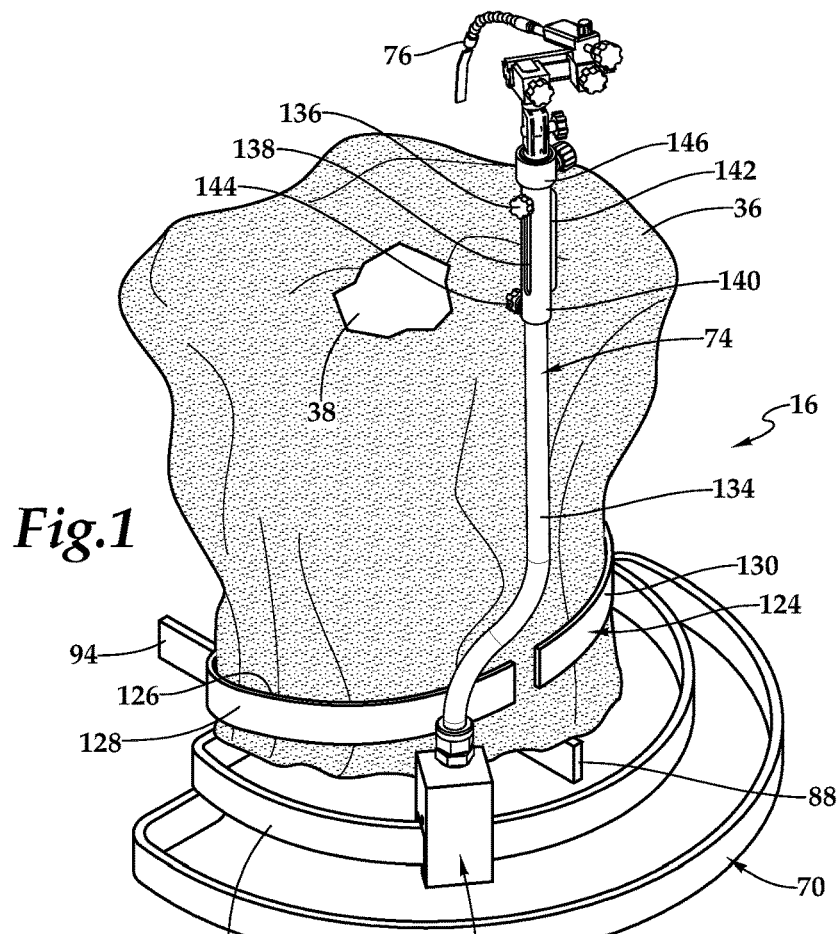
FIG. 1 is a cephalic dorsal perspective view of one embodiment of an operating room table, which is draped, with a surgical universal headrest and a base station assembly to stabilize the patient's head and facilitate the use of various surgical accessories, such as brain retractors, a surgical arm rest, and an image guidance reference frame during a surgical operative procedure on the skull and brain of a patient, according to the teachings presented herein.
Figure 2:
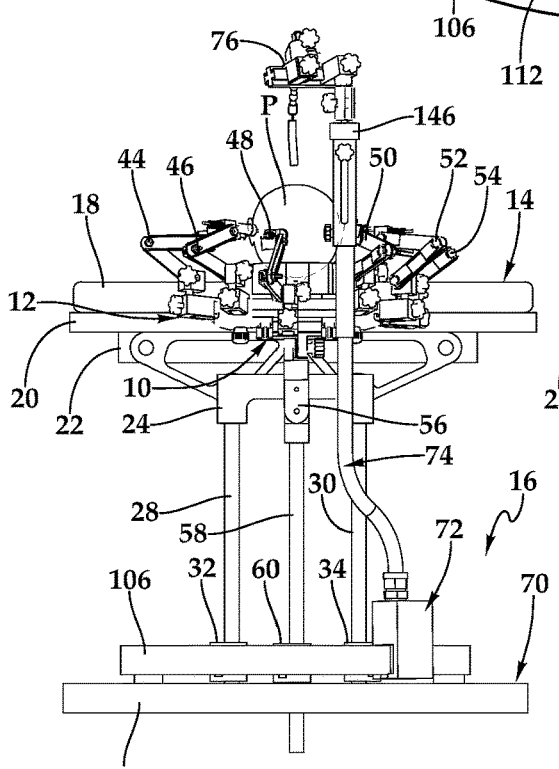
FIG. 2 is a cephalic elevation view of one embodiment of the operating room table, which is undraped, with the surgical universal headrest and the base station assembly to facilitate the use of a brain retractor during the surgical procedure, according to the teachings presented herein.
Figure 3:
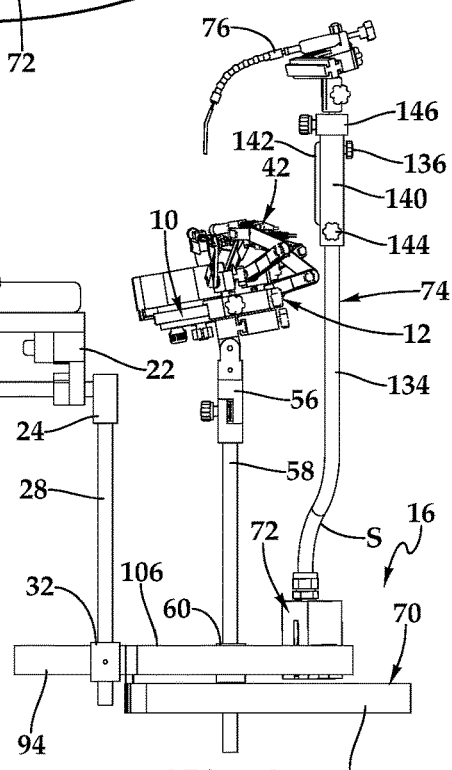
FIG. 3 is a lateral elevation view of the operating room table with the surgical universal headrest, the base station assembly with a brain retractor as depicted in FIG. 2, but without the patient.
Figure 4:
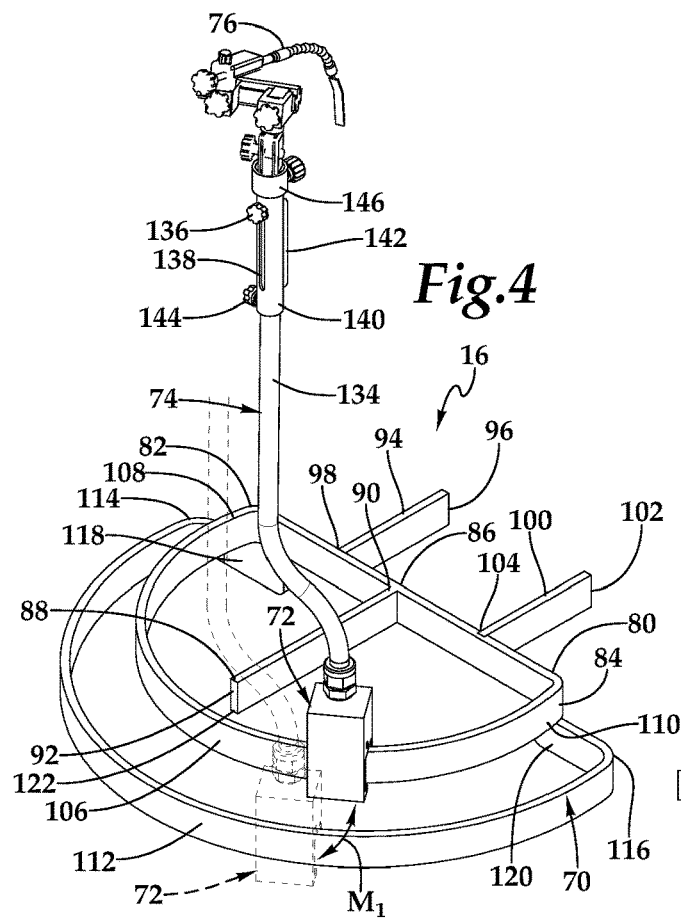
FIG. 4 is a cephalic dorsal perspective view of the base station assembly depicted in FIG. 2, without the universal headrest, its support by the base station, and the patient.
Figure 5:
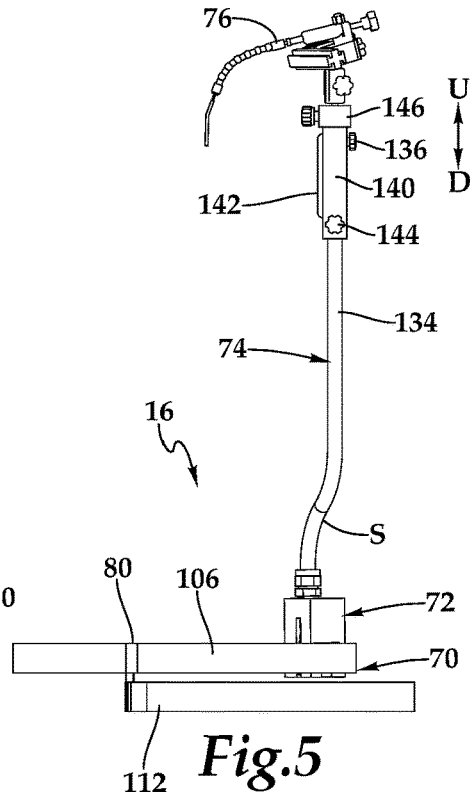
FIG. 5 is a lateral elevation view of the base station assembly supporting a brain retractor as depicted in FIG. 4.

While the making and using of various embodiments of the present invention are discussed in detail below, it should be appreciated that the present invention provides many applicable inventive concepts which can be embodied in a wide variety of specific contexts. The specific embodiments discussed herein are merely illustrative of specific ways to make and use the invention, and do not delimit the scope of the present invention.

Referring initially to FIG. 1 through FIG. 6, therein is depicted one embodiment of a surgical universal headrest 10 being utilized as a component of a surgical head holder 12 with an operating room table 14 as well as a base station assembly 16. The surgical universal headrest 10, the surgical head holder 12, the operating room table 14, and the base station assembly 16 may be utilized for skull stabilization during a surgical operation, such as neurosurgical, otolaryngological, and orthopedic procedures, for example. As will be discussed in further detail hereinbelow, the surgical universal headrest 10 is configured to support a patient ranging from a premature infant to an adult, during a surgical procedure, such as an operative microsurgical procedure on a skull and brain.

The operating room table 14 provides the surgical equipment necessary on which a patient P lies during the surgical operation. As shown, the operating room table 14 includes an operating room table pad 18 supraposed to an operating room tabletop 20 including a support block 22 connected to a support block 24 by a horizontal support member 26. Vertical support members 28, 30 extend ventrally from the support block 24 with the vertical support member 28 having a support block 32 and the vertical support member 30 having a support block 34. The support blocks 22, 24, 32, 34 may each be selectively adjustable with knobs (not shown) to assist surgical staff with proper alignment and placement of the components of the base station assembly 16, the surgical universal headrest 10, and various surgical accessories on the operating room table 14. By way of example, the support blocks 32, 34 provide for alignment and placement in the dorsal-ventral direction as well as the caudal-cephalic direction. As shown, a surgical drape 36 is draped over a head of the patient P. The surgical drape 36 has a surgical field opening 38 providing access to the head of the patient P. It should be appreciated that although one embodiment of the operating room table 14 is illustrated and described, the teachings presented herein are applicable to other operating room table configurations and designs.

The surgical head holder 12 includes the surgical universal headrest 10 that generally functions in a plane approximately parallel to the top of the operating room table 14; although, the surgical universal headrest 10 may be tilted as necessary. The surgical universal headrest 10, which will be described in much more detail hereinbelow, may carry the weight of a head of the patient P. The surgical head holder 12 includes a skull pin holder assembly 42 having skull pin holders 44, 46, 48, 50, 52, 54, or more, depending on the thinness of the patient's skull. The skull pin holder assembly 42 contributes to preventing any movement of the head of the patient P, thereby allowing safe microsurgery and enabling accurate employment of image guidance technology. As shown, the surgical universal headrest 10 is supported by a support block 56 having a vertical support member 58 extending therefrom that connects to the base station assembly 16 with the use of a support block 60. The support blocks 56, 60 may each be selectively adjustable with knobs (not shown) to assist surgical staff with proper alignment and placement of the components of the surgical head holder 12. It should be appreciated that although one embodiment of the surgical head holder 12 is illustrated and described, the teachings presented herein are applicable to other operating room table configurations and designs.

Referring now to FIG. 1 through FIG. 8, in some embodiments, the base station assembly 16 includes a base station 70 having a selectively moveable clamp 72 attached thereto. The selectively moveable clamp 72 has a vertical support arm 74 extending therefrom. The vertical support arm 74 may include a short, tight "S" curve S to assist in positioning of the vertical support arm 74 and a surgical accessory 76 attached thereto. That is, the vertical support arm 74 extends from the selectively moveable clamp 72 to provide selective attachment to the surgical accessory 76 such as a retractor arm, armrest, or image guidance frame, for example.

In one implementation, the base station 70 includes a horizontal support member 80 having ends 82, 84 with a midpoint 86 therebetween. A horizontal support member 88 has ends 90, 92. The end 90 of the horizontal support member 88 is coupled to the midpoint 86 of the horizontal support member 80 such that the horizontal support member 88 is perpendicular to the horizontal support member 80 and secured to the horizontal support member 80 at a position offset from a center T. A horizontal support member 94 includes ends 96, 98 with the end 98 being connected to the horizontal support member 80 between the end 82 and the midpoint 86. As shown, the horizontal support member 94 extends caudally from the horizontal support member 80 such that the horizontal support member 94 is perpendicular to the horizontal support member 80. Similarly, a horizontal support member 100 includes ends 102, 104 with the end 104 being connected to the horizontal support member 80 between the end 84 and the midpoint 86. As shown, the horizontal support member 100 extends caudally from the horizontal support member 80 such that the horizontal support member 100 is perpendicular to the horizontal support member 80. The horizontal support members 94, 100 of the base station 70 join the base station assembly 16 to the operating room table 14. More particularly, in one embodiment, the horizontal support member 80 is joined to the vertical support member 28 at the support block 32 and the horizontal support member 100 is joined to the vertical support member 30 at the support block 34.

An arcuate rail member 106, which may be an upright bar in cross-section, includes a radius $r_1$, as measured from the center T, and ends 108, 110. The end 108 is coupled to the end 82 of the horizontal support member 80 and the end 110 is coupled to the end 84 of the horizontal support member 80. The vertical support member 58 is secured to the horizontal support member 88, which is off center with respect to the center T, such that the vertical support member 58 is positioned at the center T. In turn, the surgical head holder 12 and the surgical universal headrest 10 are positioned at the center T with various surgical accessories positionable and repositionable, at the surgeon's discretion, via the base station assembly 16 around the center T.

A second arcuate rail member 112, which may also be an upright bar in cross-section, includes a radius $r_2$, as measured from the center T, and ends 114, 116. The end 114 is coupled to the end 82 of the horizontal support member 80 at a ventral tab 118 and the end 116 is coupled to the end 84 at a ventral tab 120 of the horizontal support member 80. The use of the ventral tab 118 and the ventral tab 120 permit the arcuate rail member 106 and the arcuate rail member 112 to be vertically offset. Importantly, as shown, a passage 122 is located between the horizontal support member 88 and the arcuate rail member 106 to provide for the movement of the selectively moveable clamp 72 around the orbit of the arcuate rail member 106.

In one implementation, the arcuate rail member 106 and the second arcuate rail member 112 are concentric. Further, the radius $r_2$ of the arcuate rail member 112 is greater than the radius $r_1$ of the arcuate rail member 106. In one embodiment of the base station 70, the arcuate rail member 106 may have an arc of about 190 degrees to about 200 degrees. In one particular embodiment of the base station 70, the arcuate rail member 106 may have an arc of about 195 degrees. In one embodiment of the base station 70, the arcuate rail member 112 may have an arc of about 205 degrees to about 215 degrees. In one particular embodiment of the base station 70, the arcuate rail member 112 may have an arc of about 210 degrees. As will be discussed in additional detail hereinbelow, it should be appreciated that depending on the embodiment selected by the surgeon, the base station 70 may have one arcuate rail member, i.e., arcuate rail member 106 or arcuate rail member 112, or the base station 70 may have two arcuate rail members, i.e., arcuate rail members 106, 112.

Figure 6:
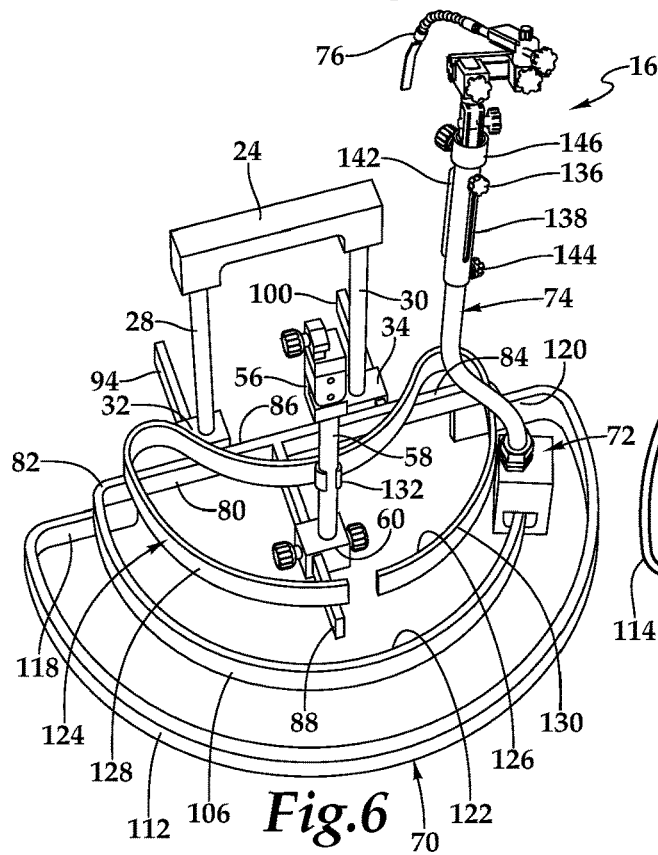
FIG. 6 is a cephalic dorsal perspective view of the base station assembly without the surgical head holder as depicted in FIG. 2, and without the patient.
Figure 8:
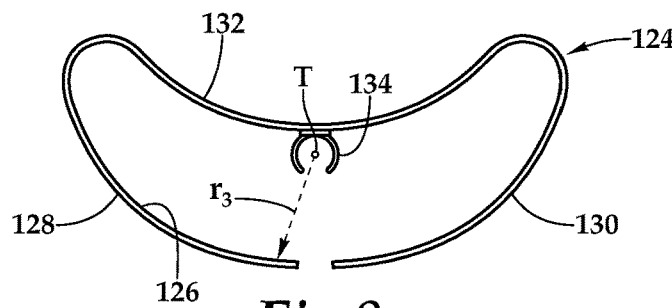
FIG. 8 is a ventral plan view of one embodiment of a drape holder depicted in FIG. 1.

As shown, the bottoms of the surgical drape 36 that fall naturally from the draping of the head of the patient are gathered and tucked inside a drape holder 124 having a symmetrically curved, oblong-shaped space 126 defined by rostral retaining members 128, 130, and a caudal retaining member 132. The drape holder 120 is adjustably secured to the vertical support member 58 by a support member 134, as best shown in FIGS. 6 and 8. In one embodiment, a radius $r_3$ of the drape holder 124 is less than the radius $r_1$ of the arcuate rail member 106 and the radius $r_2$ of the arcuate rail member 112. This permits the surgical drape 36 to be gathered and groomed so as not to interfere with the surgical procedure or use of the base station assembly 16.

The vertical support arm 74 includes an elongated member 134 that is configured to selectively actuate between a release position and an engagement position by actuation of a control knob 136. In the release position, the selectively moveable clamp 72 is actuated to an open position where the selectively moveable clamp 72 may slide on the arcuate rail member 106 and be repositioned. On the other hand, in the engagement position, the selectively moveable clamp 72 is in a closed position and locked in position on the arcuate rail member 106. The control knob 136 is located within a vertical slot 138 of a cylinder sheath 140 that contains the top end of the elongated member 134. A cabined recess 142, which is depicted as presenting a bulge, may be positioned opposite to the vertical slot 138 to accept and house the distal end of the control knob 136. A control knob 144 may provide adjustment by permitting a height of the vertical arm support 74 to be raised or lowered by adjusting a position of the cylinder sheath 140. Attachment at a coupling assembly 146 of the vertical support arm 74 provides a coupling to the surgical accessory 76.

In some operational implementations, the base station assembly 16 supports various surgical accessories during a surgical procedure, such as an operation on the skull and brain. The base station 70 provides an orbit about the surgical universal headrest 10 for the selectively moveable clamp 72 to be adjustably positioned by actuation of the control knob 126 within the vertical slot of the cylinder sheath 132 on the vertical support arm 74. Additionally, the height of the vertical support arm 74 may be adjusted as required via the control knob 144 to provide up-down U-D movement. Furthermore, the vertical support arm 74 can be selectively rotated and/or tilted slightly at its connection to the selectively moveable clamp 72 as shown by the curve S. Because of the curved geometry of the vertical support arm 74, both such maneuvers respectively move the supported surgical accessory closer or farther away from the operative site. This versatility in positioning mitigates spatial restrictions while providing enhanced surgeon control without the required assistance of others who are not scrubbed and without increased risk of contamination of the surgical field.

Figure 9:
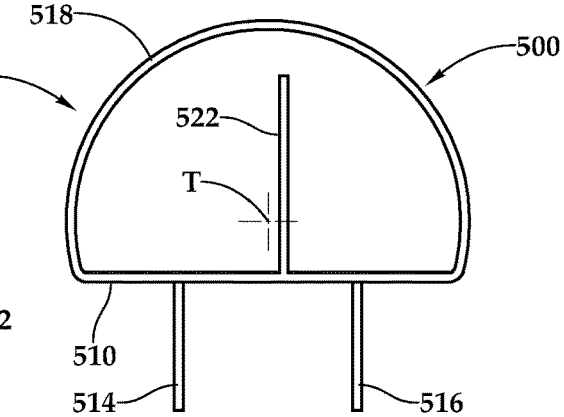
FIGS. 9 through 11 respectively represent a composite of ventral plan views of three base station embodiments, including a single rail device configuration, a double rail device configuration, and a larger center point device configuration; each being enclosed in a dimensioned rectangle, and the center points of the arcuate rails being indicated.
Figure 10:
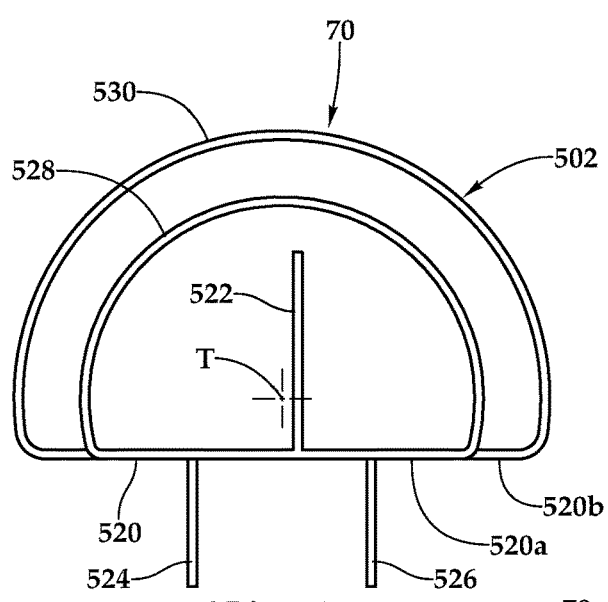
Figure 11:
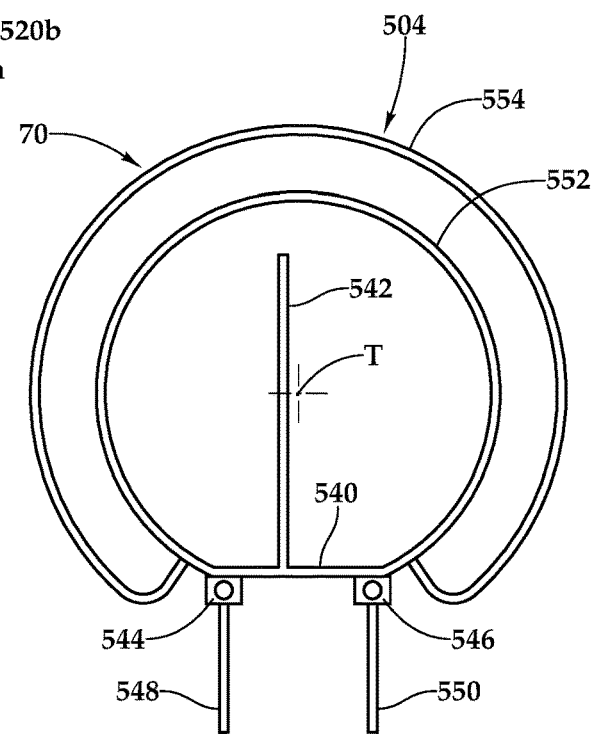
Figure 12:
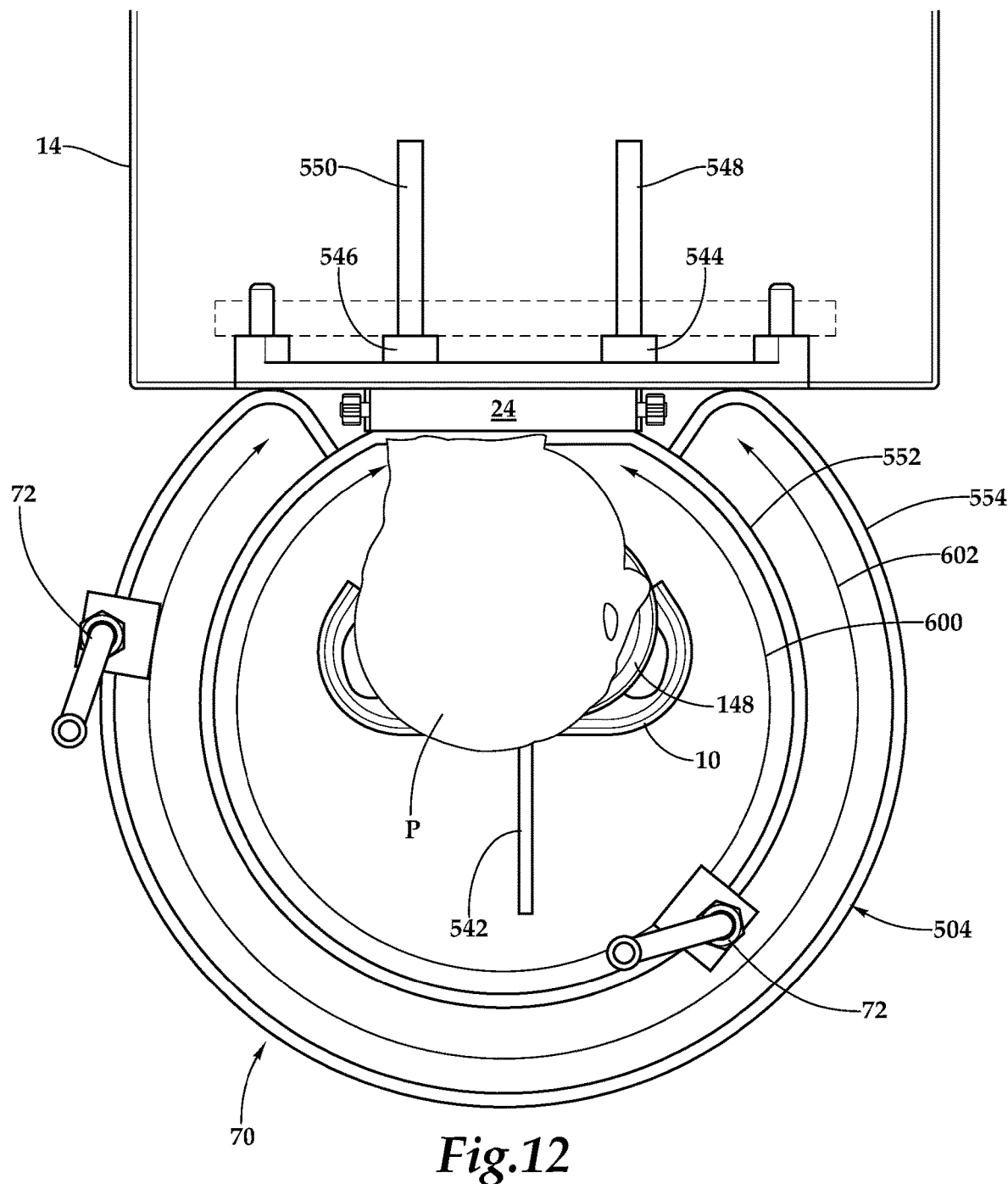
FIG. 12 is a ventral plan view of the larger center point base station depicted in FIG. 11, on which an adult patient is represented in a lateral surgical position on the surgical head holder (without skull pin fixation for clarity), wherein a selectively moveable clamp being attached to each of two concentric arcuate rails with maximal clamp excursions on the rails being indicated by hatched arrows.

Referring now to FIGS. 9, 10, and 11, as previously mentioned, other embodiments of the base station assembly 16 are within the teachings presented herein. In FIGS. 9, 10, and 11, the relative footprints of a single rail base station configuration 500, a double rail base station configuration 502, and a center point base station configuration 504 are comparatively shown together, each base station respectively contained within a dimensioned rectangle. In one such embodiment, the base station assembly 16 may have a larger presentation as indicated by center point base station configuration 504.

Figure 7:
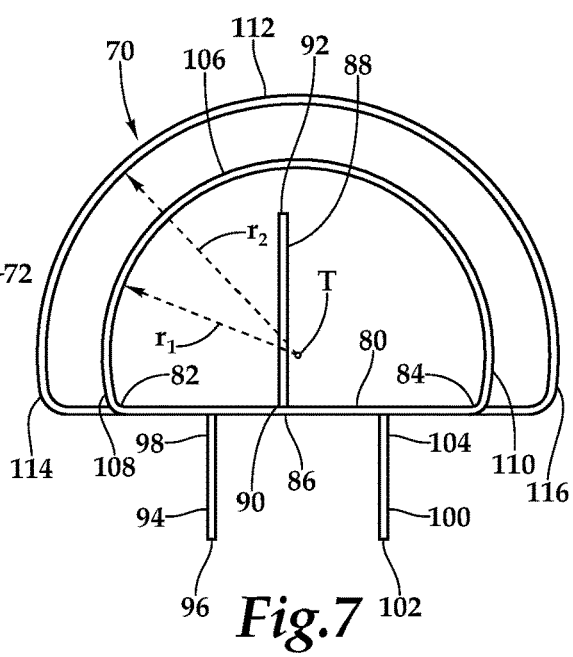
FIG. 7 is a ventral plan view of one embodiment of a base station, which forms a portion of the base station assembly depicted in FIG. 2.

Referring now to FIG. 9, in another implementation, the base station 70, which is similar to the configuration introduced in FIG. 7, includes a horizontal support member 310. In this implementation, a single orbit for the selectively moveable clamp 72 is provided. A horizontal support member 512 is coupled the horizontal support member 510 such that the horizontal support member 512 is perpendicular to the horizontal support member 510. Horizontal support members 514, 516 of the base station 70 join the base station assembly 16 to the operating room table 14. An arcuate rail member 518 is coupled to the horizontal support member 510.

Referring now to FIG. 10, in another implementation, the base station 70 includes a horizontal support member 520, which may include horizontal support submembers 520-*a*, 520-*b*. A horizontal support member 522 is coupled to the horizontal support member 520 such that the horizontal support member 522 is perpendicular to the horizontal support member 520. Horizontal support members 524, 526 of the base station 70 join the base station assembly 10 to the operating room table 12. Arcuate rail members 528, 530 are coupled to the horizontal support member 520 to, in this implementation, provide two orbits for the selectively moveable clamp 72.

Referring now to FIG. 11, in another implementation, which is like the configuration introduced in FIG. 7, the base station 70 includes a horizontal support member 540. A horizontal support member 542 is coupled to the horizontal support member 540 such that the horizontal support member 542 is perpendicular to the horizontal support member 540. Blocks 544, 546 have horizontal support members 548, 550 of the base station 70 to join the base station assembly 10 to the operating room table 12. Arcuate rail members 552, 554 are coupled to the horizontal support member 540 to, in this implementation, provide two orbits for the selectively moveable clamp 72.

Referring again to FIG. 9 through FIG. 11, in embodiments with two arcuate rail members, the arcuate rail members are concentric with the center T. Further, in some implementations, the arcuate rail members have different radii, with as shown in FIG. 10 and FIG. 11, one radius is greater than the other. As shown in FIG. 9 through FIG. 11, in some embodiments, the horizontal support member passes proximate to the center T or may be offset from the center T by a distance to accommodate a surgical head holder. It should be appreciated, however, that in other embodiments, depending on the design of the surgical head holder, the horizontal support member may pass through the center.

Further, two of the three base station devices (FIG. 10 and FIG. 11) have two arcuate rails on which one or more selectively moveable clamps 72 may be placed to support retractor arms, image guidance, and/or a surgical armrest which can be moved around the axis of the center point T of each of the respective base stations. Indeed, it is suggested that surgeons who do microneurosurgery intuitively position their patients in a surgical headrest attached to the OR table so that the surgical field, the operative target, and the actual surgical approach can all be adequately visualized with the operating microscope. Moreover, a microsurgeon would likely not operate if the head position cannot be rigidly stabilized. Accordingly, these three base station embodiments of FIGS. 9, 10, and 11 not only provide cranial stabilization utilizing the surgical head holder 12 with multiple low-pressure, but also allow efficient and reliable positioning and repositioning of brain retractors and/or a surgical armrest.

Now referring to FIG. 9 through FIG. 12, it is apparent that the center point base station configuration 504 increases the arcuate limits of both the upper and lower rails. Like the single rail base station configuration 500 and the double rail base station configuration 502, the center point base station 504 attaches to the OR table 14, utilizing the horizontal support member which receives the two horizontal rods that adjustably attach to the operating room table 14. Using the center point base station configuration 504 for patients ranging from children to adults, provides a maximal arcuate excursion of, by way of example, 286° of mobility for the selectively moveable clamp 72 on the upper arcuate rail 552 and, by way of example, a 274° excursion on the lower arcuate rail 554, as summarized in FIG. 12, with the mobility illustrated by arrows 600, 602. As shown, the selectively moveable clamp 72 is appropriately positionable and repositionable about the patient P resting on a gel pad assembly 148 of the surgical universal headrest 10.

Figure 13:
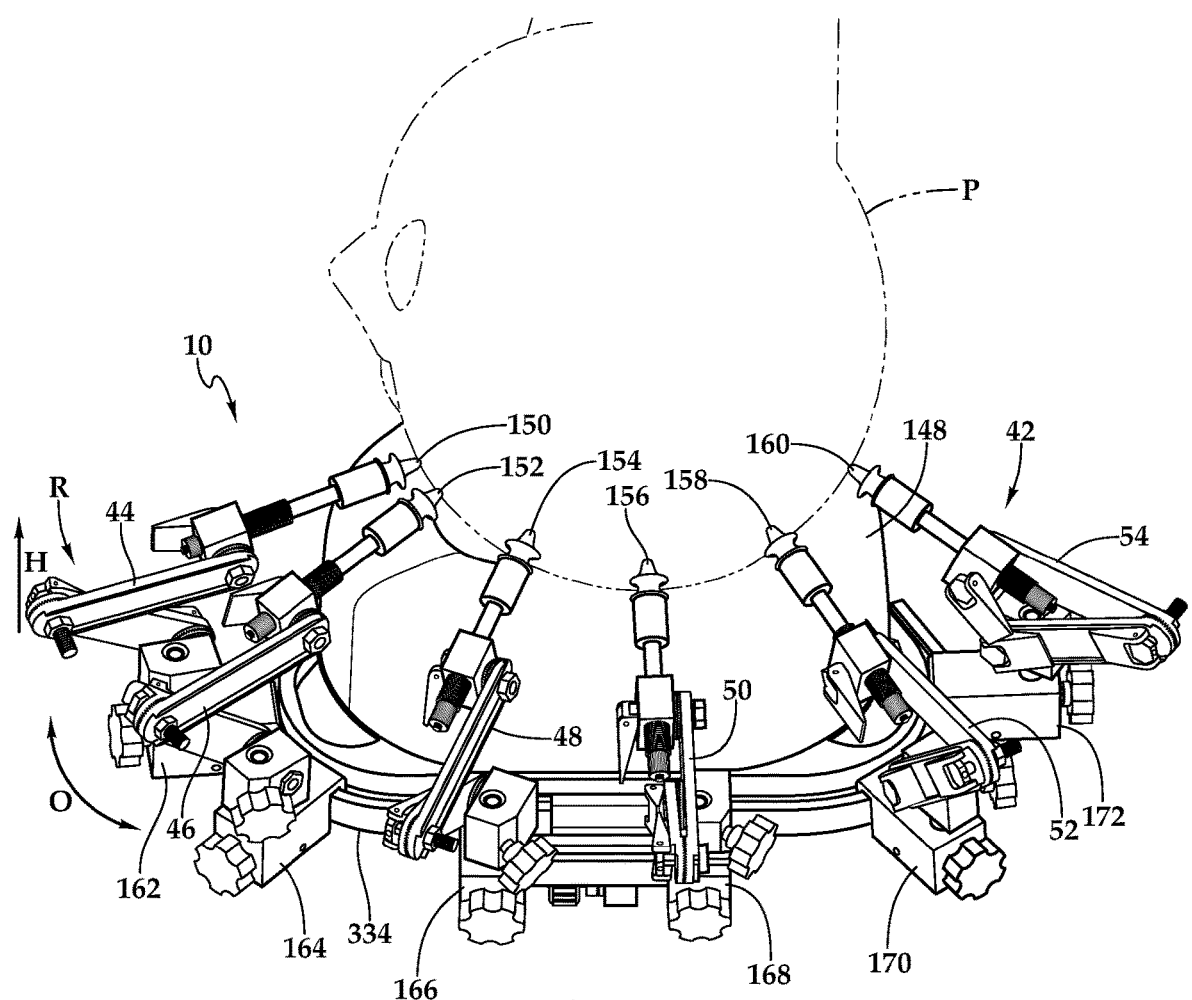
FIG. 13 is a dorsal plan view of the surgical head holder shown as the surgical universal headrest depicted in FIG. 2, with the patient.

Referring now to FIG. 13 through FIG. 15, the surgical universal headrest 10 supports the gel pad assembly 148 upon which the head of the patient P rests. The gel pad assembly may include forehead gel pads, maxillary gel pads, round gel pads, and oval gel pads, for example. It should be appreciated that the selected configuration of gel pads in the gel pad assembly will vary depending on the patient and surgical procedure. The skull pin holders 44, 46, 48, 50, 52, 54 having respective pins 150, 152, 154, 156, 158, 160 are secured to the surgical universal headrest 10 by respective locking blocks 162, 164, 166, 168, 170, 172 in a geometric arrangement around the head of the patient P so that when the respective pins 150, 152, 154, 156, 158, 160 are tightened at low pressure, the pins 150-160, collectively, prevent movement of the head of the patient P in space as required by surgical procedures. High pin pressures are not required as the weight of the head of the patient P is not being supported by the pins 150-160; rather, the weight of the head is supported by the surgical universal headrest 10, which is designed to carry strong structural parts of the skull and facial skeleton of the patent P with the gel pad assembly 148, which may include one or more gel pads.

With reference to FIGS. 14 and 15, the skull pin holders 44, 46, 48, 50, 52, 54, or more, having pins 150, 152, 154, 156, 158, 160, or more, may utilize either a mechanical measure of pin pressure or, as in another embodiment, a pin assembly that utilizes wireless communication to facilitate the measurement and monitoring of pin pressure. In FIGS. 14 and 15, the skull pin holder 44 having pin 150 is presented in further detail as a non-limiting example. The pin 150 having a tip 177 is held in position by a pin cup 178 extending from a shaft 179 having a threaded barrel 180 for threadably engaging a locking block 181. The threaded barrel 180 also includes a finger knob 182 for tightening or loosening the pin 150. A housing 196 is secured to the end of the threaded barrel 180. Positioning arms 183, 184 with lock levers 185, 186, 187 secure the locking block 181 to a locking block 188, which includes an adjustment knob 189. A channelized block 190 having a knob 191 secures the skull pin holder 44 to a portion of the surgical universal headrest 10, as will be described in further detail hereinbelow.

Within the pin cup 178, a base 192 of the pin 150 is secured to a micro strain measuring device 193, which measures the strain and therefore provides an indication of the pressure force exerted onto the skull of the patient P. More particularly, the micro strain measuring device 193, which may be a strain gauge, including a micro-strain gauge, for example, is positioned proximate a floor of the pin cup 178, to electronically measure resistance within a grid within the micro strain measuring device 193 that results from grid deformation caused by forces exerted by the base of the skull pin 150 pressing on the respective strain gage grid, from which pin pressure can be determined. In another embodiment, the micro strain measuring device 193 may be alternatively positioned on a planar surface cut into the proximal pin arm 179 with the linear grid parallel to the center axis of the pin arm 179. It should be appreciated, however, that the micro stain measuring device 193 may be any form of measuring device that includes strain gauge load cells or force sensors. In some embodiments, the micro strain measuring device 193 is connected by a wire 194 to transmitter 195 housed within the housing 196.

The electronic data from the strain gauge 193 is wirelessly transferred to an electronic monitor (not shown) that may be positioned close to the patient's head, such as on display with the anesthesia monitors, for example. The transmitter 195 may be enabled by a variety of wireless methodologies, including 802.11, 3G, 4G, Edge, WiFi, ZigBee, near field communications (NFC), and Bluetooth, for example. The monitor transforms the resistance data to determine the pin pressure at each pin. The monitor displays the pressure either digitally and/or graphically, and both audio and visual alarms may alert the surgeons that the pin pressure for a specific skull pin, such as skull pin 150, 152, 154, 156, 158, 160, or more has increased or decreased out of an acceptable range, thereby indicating the likelihood of a problem. These measurements may be invaluable in the process of the initial finger-tightening of the skull pins 150, 152, 154, 156, 158, 160, or more. Moreover, during the surgical procedure, a skull pin pressure that drops significantly below the original placement pressure may indicate that the pin has penetrated or deformed the skull—a significant complication of very small children, infants, and babies. The surgeon may wish to examine the pin of concern and decide how to manage the situation.

There are commercially available skull pins for adults, and drawings are shown in the aforementioned FIGS. 14 and 15. In addition, there are so-called "pediatric" skull pins for children, on which the point of the pin has a center axis that measures approximately 3.5 mm in length, and at the base of the point, there is a radial collar that measures approximately 11 mm in diameter. Either type of skull pin may be used with the surgical universal headrest 10, and the neurosurgeon should decide which type of pin would be appropriate for a particular patient.

In one implementation, for patients who are adults or teenagers, it is likely that only four (4) to six (6) pins will be required at low pressure to prevent movement, although there is no problem with using more. As shown in FIG. 13, the patient P is an adult requiring six (6) pins, the aforementioned pins 150-160. For patients that are small children or infants, eight (8) to ten (10) pins are suggested as the skull is significantly thinner than those of adults and the skull may deform, fracture, or allow pin penetration. For an even smaller patient P, ten (10) to twelve (12) pins may be required. The thinner and more delicate the cranial vault, the greater number of low-pressure pins are required to achieve safe immobility of the head of the patient P.

In some operational embodiments, the skull pin holder assembly 42 provides the multiple skull pin holders 44-46 that, with skull pin holder 44 as an example, have the pin 150 with the tip 177 and the base 192. The micro strain measuring device 193 is coupled to the base to, as previously discussed, electronically measure resistance resulting from forces exerted at the interface of the pin 150 and the skull of the patient P. As discussed, the micro strain measuring device 193 outputs electronic data relative thereto. More specifically, the transmitter 195 is communicatively coupled to the micro strain measuring device 193 to wirelessly transmit the electronic data to a computing device, for example, to provide a readout in the OR of the pressure each pin 150, 152, 154, 156, 158, 160, for example, is exerting. As a result, appropriate adjustments may be made. The positioning arms 183, 184 and the locking blocks 181, 188, 190 mechanically support a position of the pin 150 with respect to rotation R and height H while the skull pin holder 44 is adjustably positioned on a rail 334 which defines at least a partial orbit O about the skull of the patient P.

Referring now to FIG. 16 through FIG. 22, the surgical universal headrest 10 includes a body 200 having a dorsal surface 202, a ventral surface 204, a lateral end 206, a lateral end 208, a caudal end 210, and a cephalic end 212. The body 200 includes a horizontal axis $A_1$ therethrough as well as a vertical axis $A_2$ therethrough. As shown, the horizontal axis $A_1$ is perpendicular to the vertical axis $A_2$ with the body 200 having a medial line M between the lateral end 206 and the lateral end 208. Extension members 214 extend from the lateral end 206 and extension members 216 extend from the lateral end 208. A block member 218 extends from the ventral surface 204 of the body 200.

A lateral wing 220 has a dorsal side 222, a ventral side 224, a proximal side 226, a distal side 228, a caudal side 230, and a cephalic side 232. The lateral wing 220 is slidably connected at the proximal side 226 to the lateral end 206 of the body 200 via the extension members 214. While continuing to refer to FIGS. 10 through 22, as best seen by comparing FIG. 16 and FIGS. 21 through 22, the lateral wing 220 has a range $R_1$ of lateral sliding motion with respect to the body 200. The lateral wing 220 includes a trough 234 defined by a sidewall 236, which may have a consistent depth, with a floor 238 and an opening 240. The trough 234 may be disposed on the dorsal side 222 of the lateral wing 220. The sidewall 236 has wall portions 242, 244, 246, 248, and 250.

A glide 252 is secured to the floor 238 of the trough 234 proximate the opening 240 between the wall portion 242 and the wall portion 250. A rail 254 extends along a periphery margin 256 of the lateral wing 220 from the distal side 228 to the cephalic side 232. The skull pin holders 44, 46, 48 are secured to the rail 254 of the surgical universal headrest 10 by the respective locking blocks 162, 164, 166 in a geometric arrangement around the head of the patient P. The skull pin holders 44, 46, 48 may be repositioned, as required, along the rail 254.

An arm 260 includes a body 262 having an upper side 264, a lower side 266, an end 268, an end 270, an inner wall member 272, and an outer wall member 274. An elongated slot 276, which may be linear slot or an arcuate slot, for example, traverses the body 272 and the elongated slot 276 includes the glide 252 therein to moveably secure the arm 260 to the trough 234. A post 278 is secured to the upper side 264 of the body 262 proximate to the end 268. Openings 280, 282 are positioned on the body 262 proximate the end 270. While continuing to refer to FIGS. 16 through 22, as best seen by comparing FIG. 16 and FIGS. 21 and 22, the arm 260 has a range of proximal-to-distal motion $R_2$ with respect to the medial line M in a caudal plane C.

A lateral wing 300 has a dorsal side 302, a ventral side 304, a proximal side 306, a distal side 308, a caudal side 310, and a cephalic side 312. It should be appreciated that the lateral wing 300 and the lateral wing 220 may comprise symmetrical forms. The lateral wing 300 is slidably connected at the proximal side 306 to the lateral end 208 of the body 200 via the extension members 216. While continuing to refer to FIGS. 16 through 22, as best seen by comparing FIG. 16 and FIGS. 21 through 22, the lateral wing 300 has a range $R_3$ of lateral sliding motion with respect to the body 200. The lateral wing 300 includes a trough 314 defined by a sidewall 316, which may have a consistent depth, with a floor 318 and an opening 320. The trough 314 may be disposed on the dorsal side 302 of the lateral wing 300. The sidewall 316 has wall portions 322, 324, 326, 328, and 330. A glide 332 is secured to the floor 318 of the trough 314 proximate the opening 320 between the wall portion 322 and the wall portion 330. As previously alluded, the rail 334 extends along a periphery margin 336 of the lateral wing 300 from the distal side 308 to the cephalic side 312. The skull pin holders 50, 52, 54 are secured to the rail 334 of the surgical universal headrest 10 by the respective locking blocks 168, 170, 172 in a geometric arrangement around the head of the patient P. The skull pin holders 50, 52, 54 may be repositioned, as required, along the rail 334.

An arm 340 includes a body 342 having an upper side 344, a lower side 346, an end 348, an end 350, an inner wall member 352, and an outer wall member 354. It should be appreciated that the arm 340 and the arm 260 may have symmetrical forms. An elongated slot 356, which may be linear slot or an arcuate slot, for example, traverses the body 342 and the elongated slot 356 includes the glide 332 therein to moveably secure the arm 340 to the trough 314. A post 358 is secured to the upper side 344 of the body 342 proximate to the end 348. Openings 360, 362 are positioned on the body 342 proximate the end 350. While continuing to refer to FIGS. 16 through 22, as best seen by comparing FIG. 16 and FIGS. 21 and 22, the arm 340 has a range of proximal-to-distal motion $R_4$ with respect to the medial line M in a caudal plane C.

Figure 16:
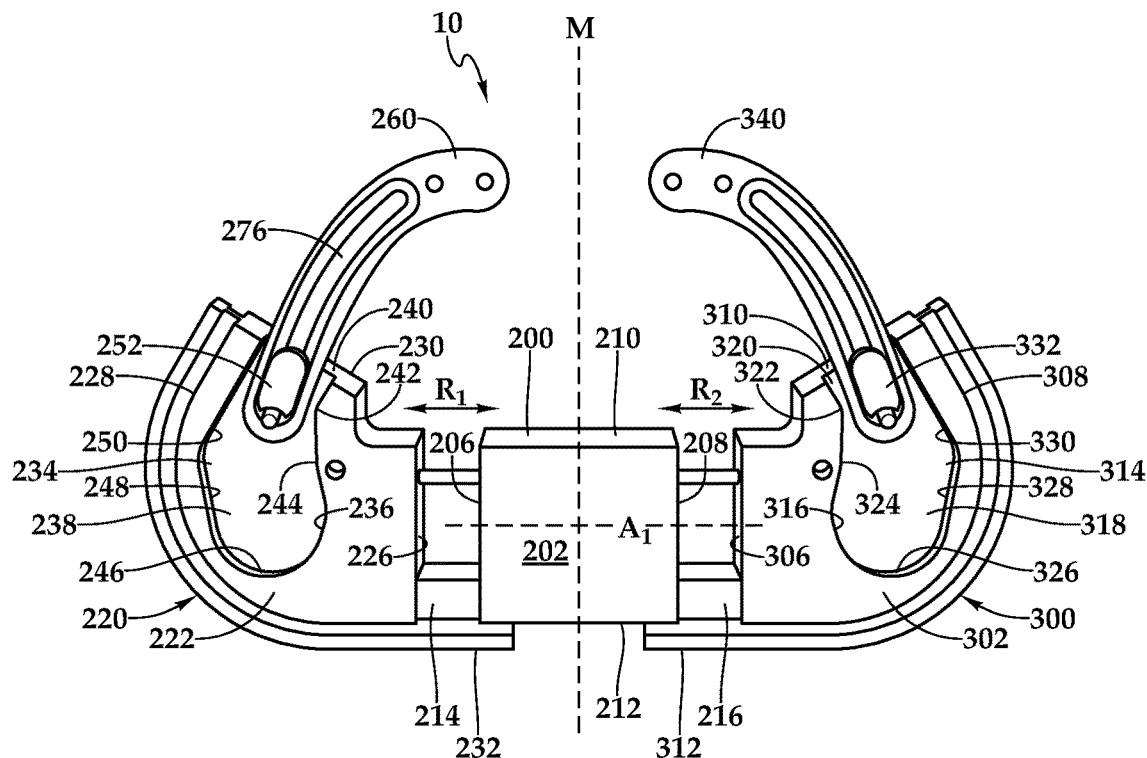
FIG. 16 is a dorsal plan view of the surgical universal headrest depicted in FIG. 2.
Figure 17:
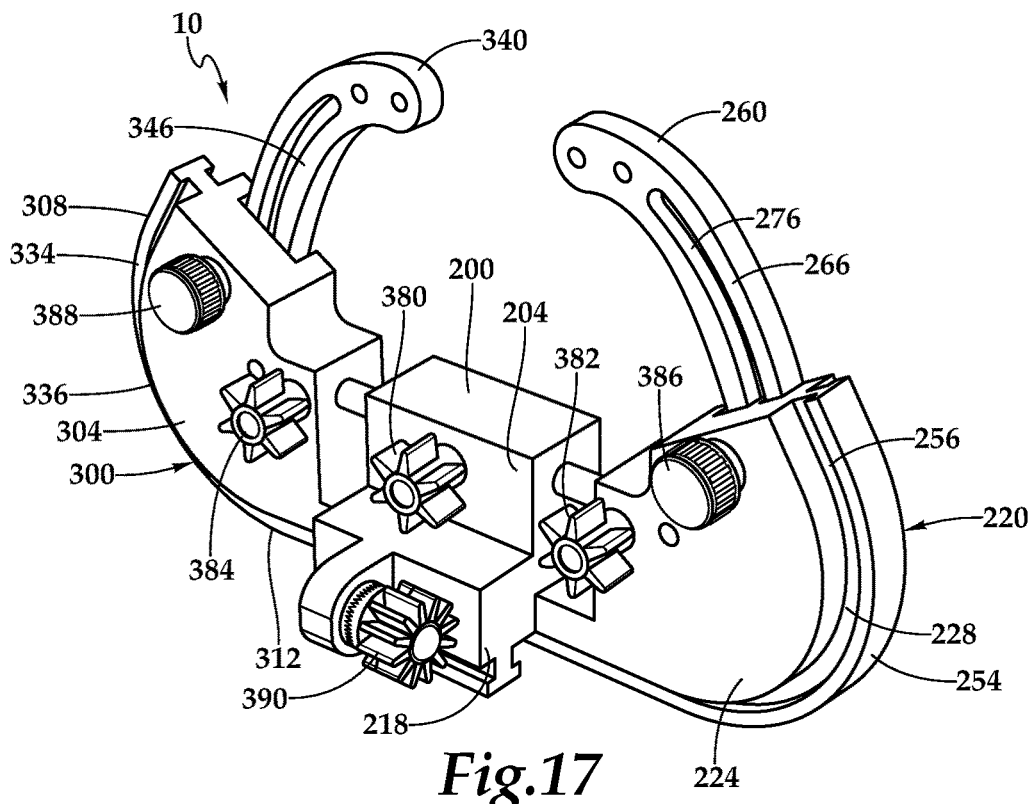
FIG. 17 is a ventral perspective view of the surgical universal headrest depicted in FIG. 16.
Figure 18:
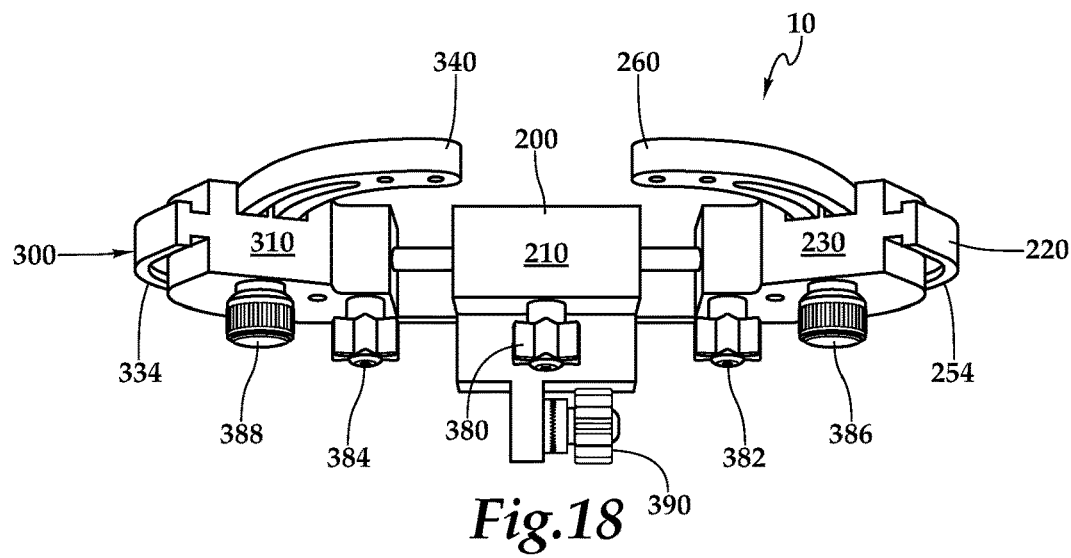
FIG. 18 is a cephalic elevation view of the surgical universal headrest depicted in FIG. 16.
Figure 19:
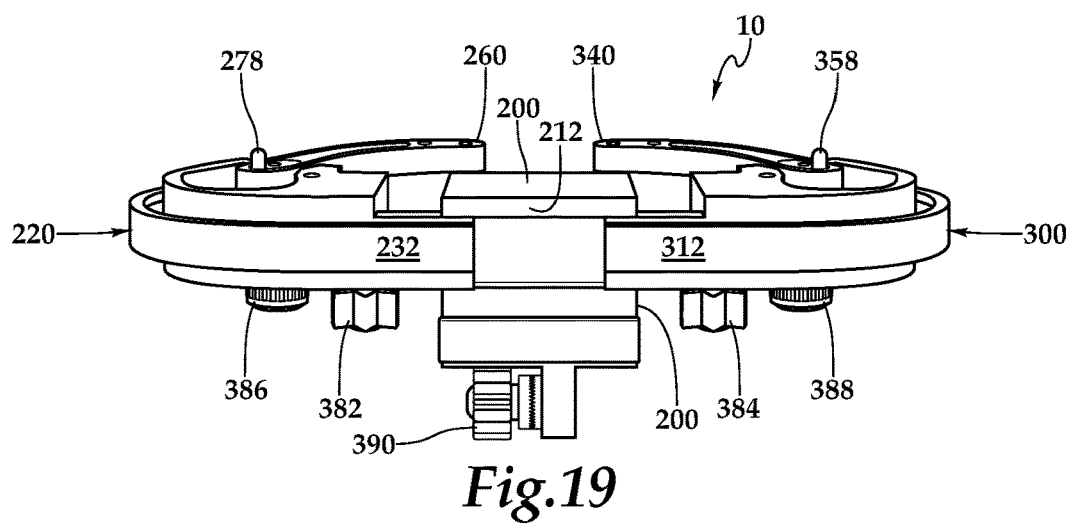
FIG. 19 is a caudal elevation view of the surgical universal headrest depicted in FIG. 16.
Figure 20:
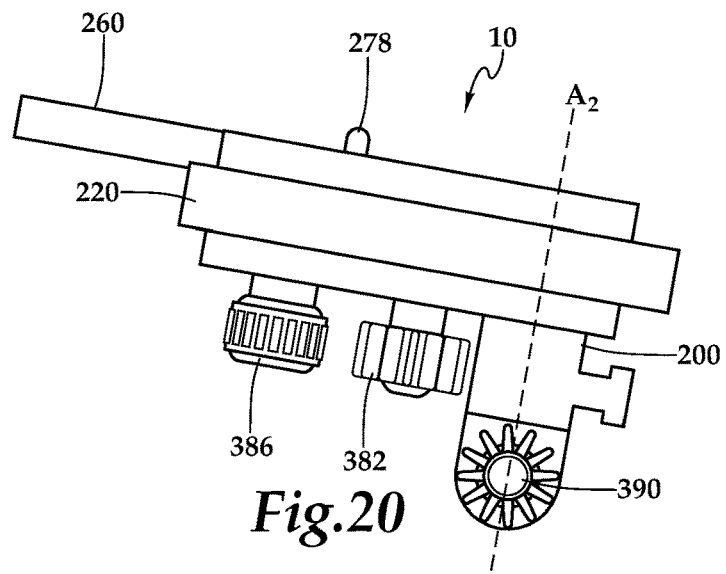
FIG. 20 is a lateral elevation view of the surgical universal headrest depicted in FIG. 16.

As shown, the body 200, the lateral wing 230, the arm 260, the lateral wing 300, and the arm 240 in cooperative combination, define a support perimeter 370, of an adjustable size, having an opening 372 therethrough. The support perimeter 370 accommodates patients ranging from premature infants to adults and the opening 372 has a size that adjusts with the support perimeter 370. To assist in this accommodation, the support perimeter 370 of the surgical universal headrest 10 is adjustable to an extended position E, wherein as best seen in FIG. 16, there is minimum relative contact between the arm 260 and the sidewall 236 as well as minimum relative contact between the arm 340 and the sidewall 316. As shown, the extended position E also has a maximum range of lateral sliding motion with respect to the body 200 and the lateral wing 230 as well as a maximum range of lateral sliding motion with respect to the body 200 and the lateral wing 300.

Figure 21:
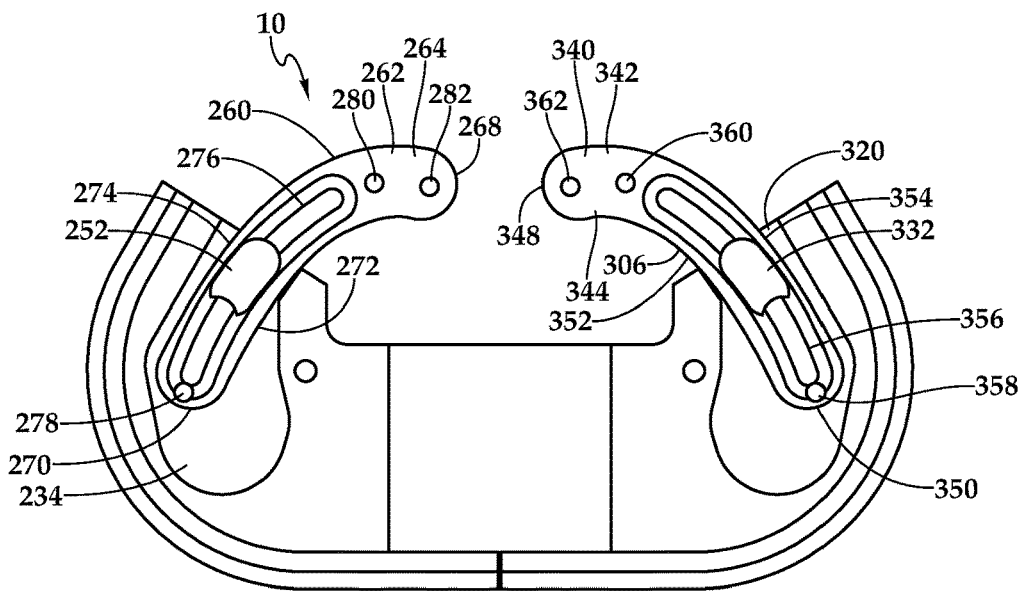
FIG. 21 is a dorsal plan view of the surgical universal headrest depicted in FIG. 16 in an alternative articulation.
Figure 22:
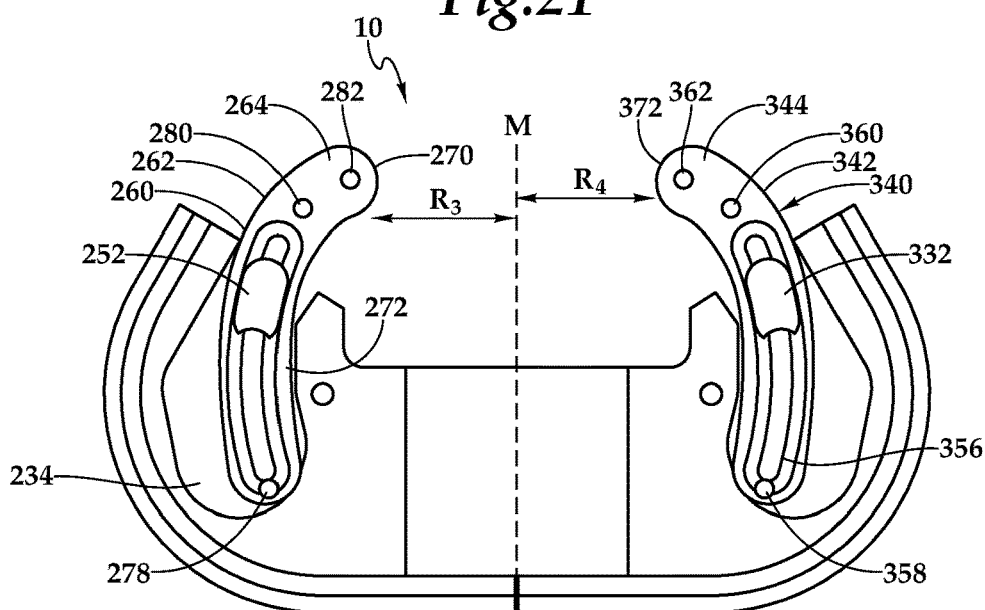
FIG. 22 is a dorsal plan view of the surgical universal headrest depicted in FIG. 16 in another alternative articulation.

While continuing to refer to FIGS. 16 through 22, as best seen in FIGS. 21 and 22, the support perimeter 320 includes a collapsed position L. In one implementation as best shown in FIG. 21, the collapsed position L includes minimal relative contact between the arm 260 and the sidewall 236 as well as minimum relative contact between the arm 340 and the sidewall 316. The collapsed position L also includes a minimum range of lateral sliding motion with respect to the body 200 and the lateral wing 230 as well as a minimum range of lateral sliding motion with respect to the body 200 and the lateral wing 300. In another implementation as best shown in FIG. 22, the collapsed position L includes maximum relative contact between the arm 260 and the sidewall 236 as well as maximum relative contact between the arm 340 and the sidewall 316. The collapsed position L also includes a minimum range of lateral sliding motion with respect to the body 200 and the lateral wing 230 as well as a minimum range of lateral sliding motion with respect to the body 200 and the lateral wing 300.

A control knob 380 coupled to the ventral surface 204 of the body 200 as well as a control knob 382 coupled to ventral side 224 of the lateral wing 220 and a control knob 384 coupled to the ventral side 304 of the lateral wing 300 determine the ranges $R_1$, $R_2$. Respective locking knobs 386, 388 of the ventral sides 224, 304 of the lateral wings 220, 300 lock the arms 260, 340 in place. A control knob 390 couples the surgical universal headrest 10 to support block 56 and, in some embodiments, controls front-back tilt with a pitch block (not shown) changing lateral tilt and rotation.

Figure 23:
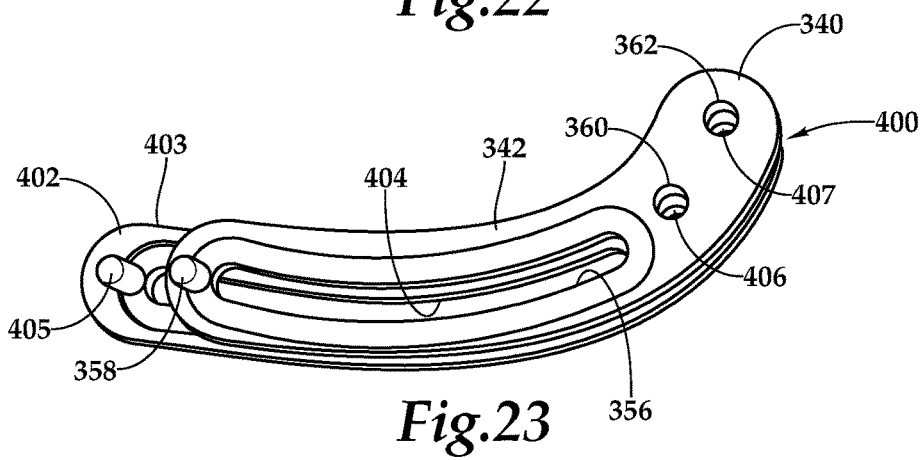
FIG. 23 is a dorsal plan view of an alternative embodiment of an arm, which forms a portion of the surgical universal headrest depicted in FIG. 2.

A number of inserts may be utilized with the surgical universal headrest 10 to enhance functionality with large patients, such as large adults, or very small patients, such as premature infants. By way of example, FIG. 23 depicts an alternative embodiment of an arm 400, which may form a portion of the surgical universal headrest 10 depicted in FIGS. 16 through 22. The arm 400 includes the arm 340 superposed on a long arm 402. With this configuration, large adults may be supported. More particularly, as previously discussed, the arm 340 includes the body 342 with the elongated slot 356 that traverses the body 342 and the elongated slot 356 may accommodate the glide 332 therein to moveably secure the arm 340 to the trough 314. A post 358 is secured to the body 342. The openings 360, 362 are positioned on the body 342. Similarly, the long arm 402 includes a body 403 with an elongated slot 404 that traverses the body 403 and the elongated slot 404 may accommodate the glide 332 therein in instances when a large adult may be supported. A post 405 is secured to the body 403 with openings 406, 407 aligned with openings 360, 362. As shown in FIG. 23, the long arm 402 extends the length o the arm 340 and adds strength thereto for accommodating a large adult.

Figure 24:
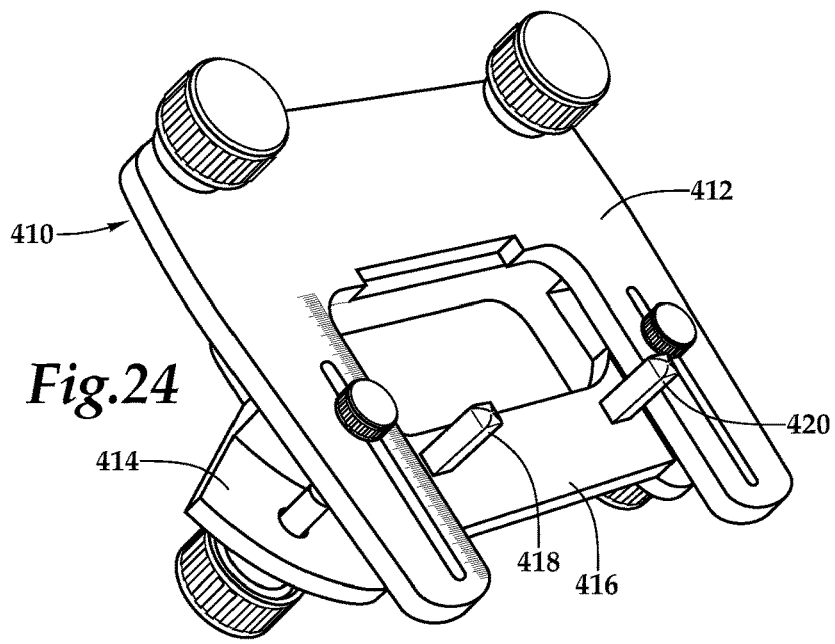
FIG. 24 is a cranial perspective view of a premature infant insert that may be utilized with the surgical universal headrest.
Figure 25:
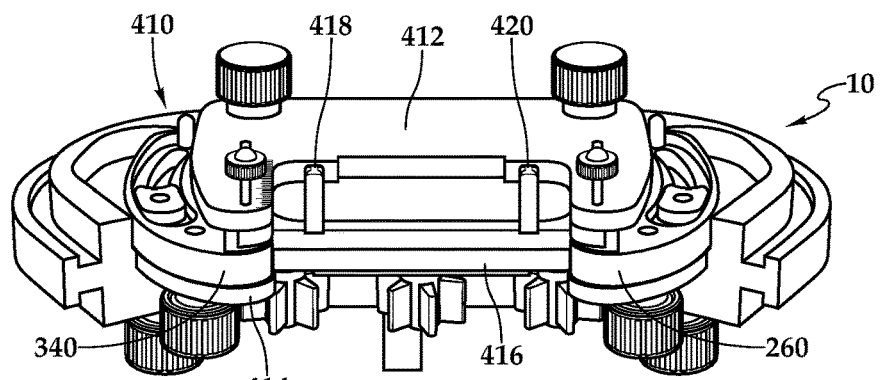
FIG. 25 is a caudal plan view of the premature infant insert depicted in FIG. 18 be utilized with the surgical universal headrest.
Figure 26:
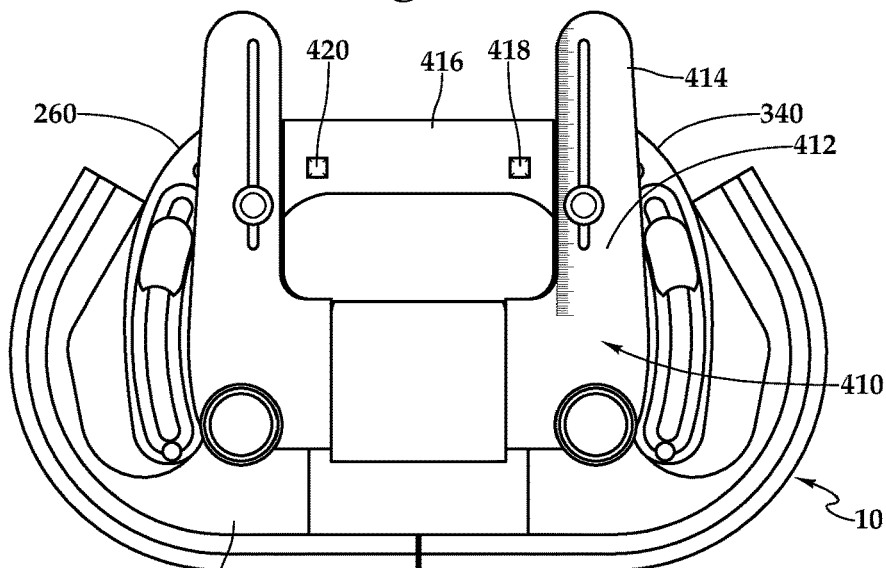
FIG. 26 is a dorsal plan view of one embodiment of the surgical universal headrest with the premature infant insert.
Figure 43:
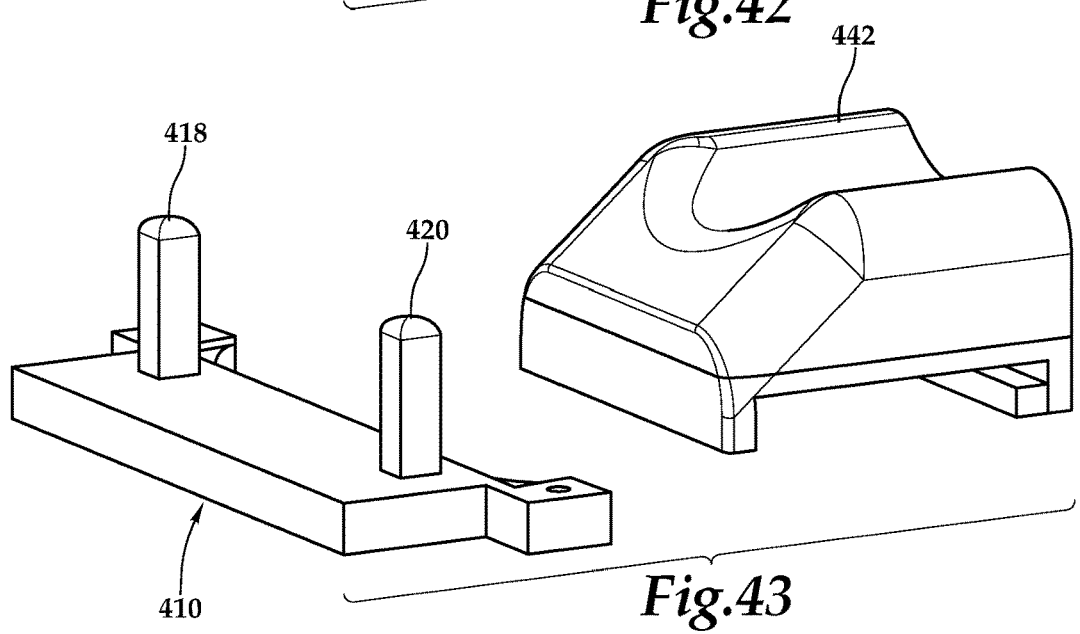
FIG. 43 is a cephalic-lateral perspective view of the bimaxillary support depicted in FIG. 36 to demonstrate the two vertical posts that support and prevent collapse of the maxillary gel pad.
Figure 44:
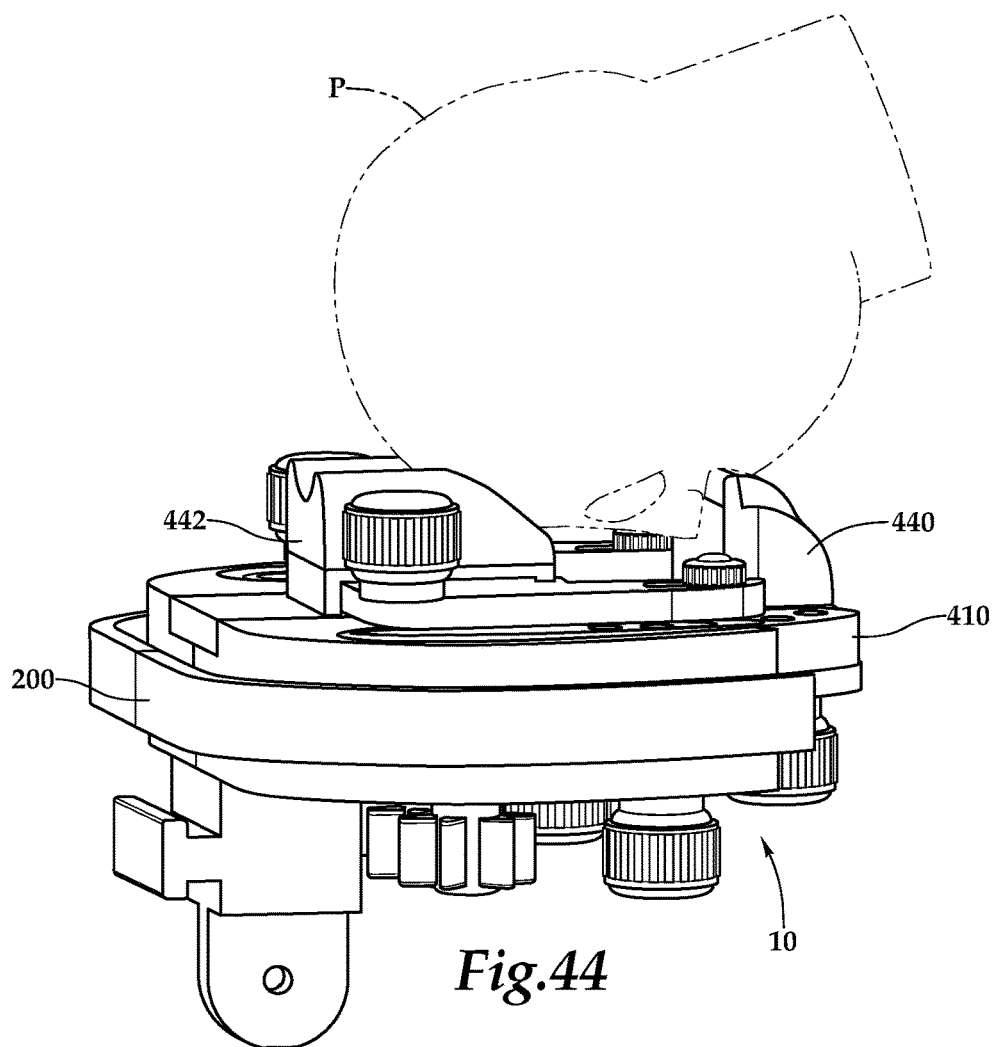
FIG. 44 is a lateral perspective view of the surgical universal headrest with the premature insert in place to perform prone surgery on a premature baby.

By way of further example, FIGS. 24 through 26 depict a premature infant insert 410 that may be utilized with the surgical universal headrest 10 depicted in FIGS. 16 through 22. The premature infant insert 410 includes an upper plate 412 superposed on a lower plate 414 with a bimaxillary support member 416 therebetween. Two maxillary support posts 418, 420 are proximate the respective suprapositions of the bimaxillary support member 416 by the upper plate 412. The maxillary support posts 418, 420 stabilize a maxillary gel pad 422 (See FIG. 43) and prevent its collapse under the weight of the patient's head.

With reference to FIG. 16 through FIG. 26, to utilize the premature infant insert 410, the surgical universal headrest 10 is placed in the collapsed position L that includes maximum relative contact between the arm 260 and the sidewall 236 as well as maximum relative contact between the arm 340 and the sidewall 316. This collapsed position L also includes a minimum range of lateral sliding motion with respect to the body 200 and the lateral wing 220 as well as a minimum range of lateral sliding motion with respect to the body 200 and the lateral wing 300.

As previously discussed, the support perimeter 370 accommodates patients ranging from premature infants to adults and the opening 372 has a size that adjusts with the support perimeter 370 to accommodate the eye and nose region of the patient P. With the universal surgical headrest 10 in the collapsed position L, the support perimeter 370 and the opening 372 are minimized. Within this minimized configuration, the premature infant insert 410 is secured to the universal surgical headrest 10 to accommodate low gestational age infants, for example.

Figure 27:
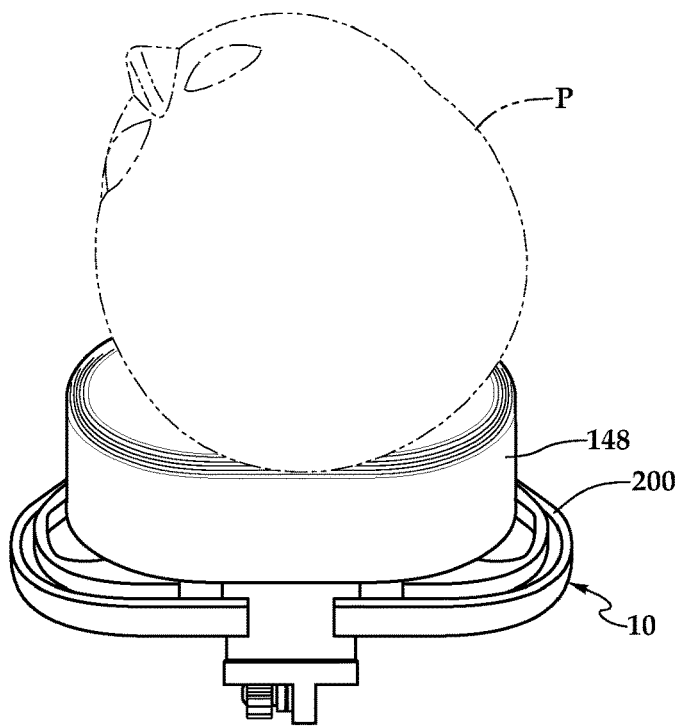
FIG. 27 is a cephalic perspective view of one embodiment of the surgical universal headrest being utilized with supine positioning of an adult patient during a surgical procedure, such as an operative procedure on a skull and brain involving a right pterional approach of the adult patient.
Figure 28:
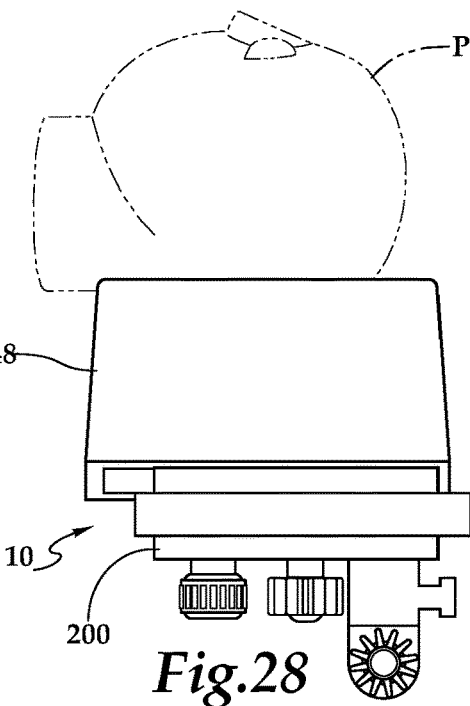
FIG. 28 is a lateral elevation view of one embodiment of the surgical universal headrest being utilized with supine positioning of a five (5)-month old child patient during a surgical procedure, such as an operative procedure on a skull and brain involving a bifrontal craniotomy of the five (5)-month-old patient.

By way of example and not by way of limitation, FIG. 27 through FIG. 32 show various configurations of the surgical universal headrest 10 with gel pad assemblies 148 for supporting the patient P. FIG. 27 through FIG. 32 show a portion of the spectrum of surgical procedures and range of gel pad assemblies 148 that may be utilized. More particularly, FIG. 27 depicts one embodiment of the universal surgical headrest 10 being utilized with supine positioning of an adult patient P during a surgical procedure, such as an operative procedure on a skull and brain involving a right pterional approach of the adult patient. FIG. 28 depicts one embodiment of the universal surgical headrest 10 being utilized with supine positioning of a five (5)-month old child patient during a surgical procedure, such as an operative procedure on a skull and brain involving a bifrontal craniotomy of the five (5)-month old patient.

Figure 29:
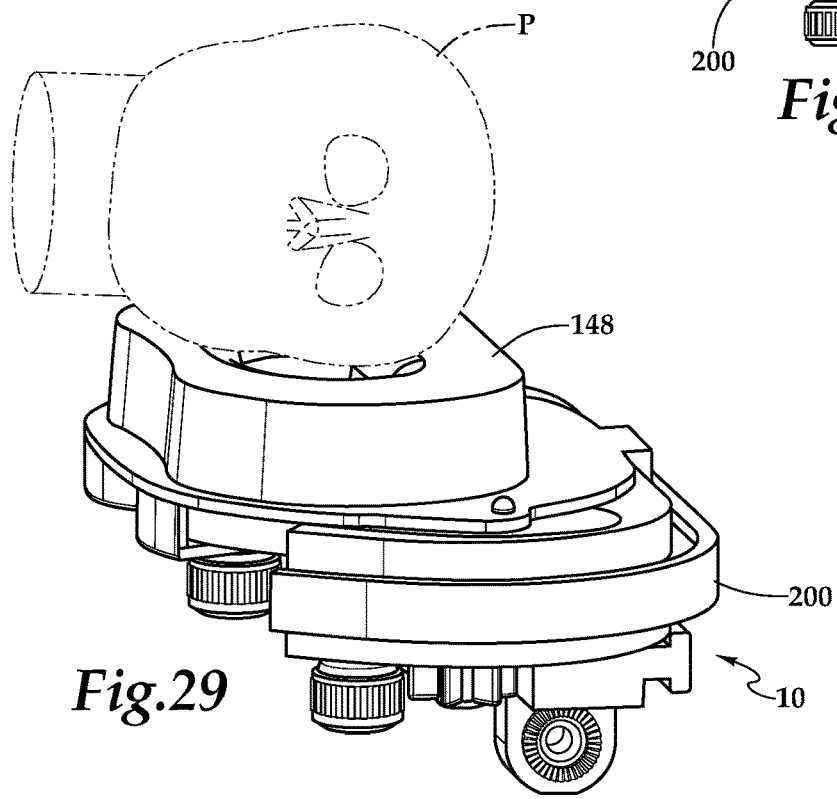
FIG. 29 is a lateral perspective view of one embodiment of the surgical universal headrest being utilized with supine positioning of a twenty-eight (28)-week gestational age patient during a surgical procedure, such as an operative procedure on a skull and brain involving a lateral approach of the twenty-eight (28)-week gestational age patient.

FIG. 29 depicts one embodiment of the universal surgical headrest being utilized with supine positioning of a twenty-eight (28)-week gestational age patient during a surgical procedure, such as an operative procedure on a skull and brain involving a lateral approach of the twenty-eight (28)-week gestational age patient. FIG. 30 depicts one embodiment of the universal surgical headrest being utilized with prone positioning of a sixteen (16)-year old patient during a surgical procedure, such as an operative procedure on a skull and brain of the patient P. FIG. 31 depicts one embodiment of the universal surgical headrest with a premature insert 410 being utilized for prone positioning of a full-term newborn patient during a surgical procedure, such as posterior fossa operation on the skull and brain of the full-term newborn patient P. FIG. 32 depicts one embodiment of the universal surgical headrest with the premature insert 410 being utilized for prone positioning of a thirty-two (32)-week gestational age baby patient during a posterior fossa operation on the skull and brain of the thirty-two (32)-week gestational age baby patient P.

Figure 33:
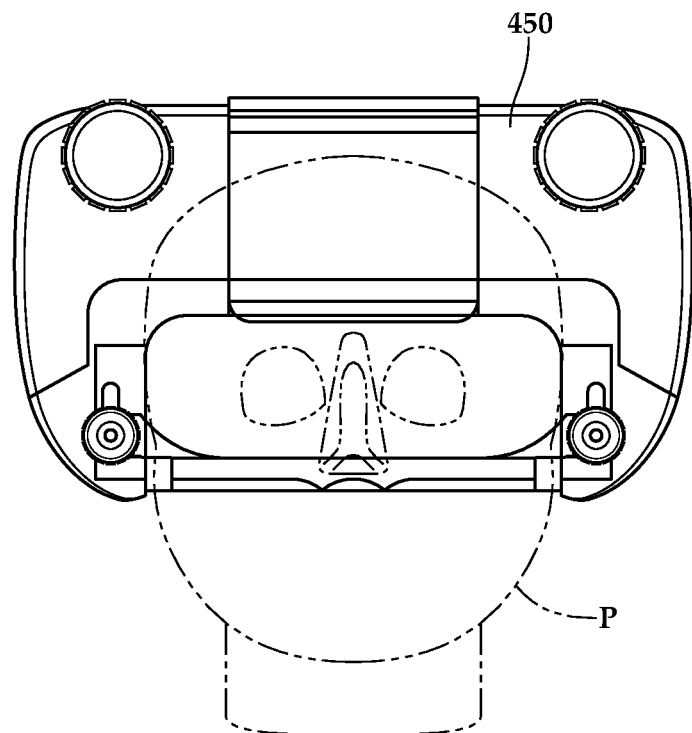
FIG. 33 is a ventral elevation view of a premature infant fitted with a transparent acrylic template for prone surgery in premature infants.

In general, in preparing the universal surgical headrest 10 for prone positioning requires that the surgeon first adjust the width of the surgical universal headrest 10 by adjusting the positioning of the lateral wings 220, 300 relative to the body 200 as well as the placement of the arms 260, 340. It is recommended that these adjustments be made before the patient is rolled into the prone position. A series of templates for prone positioning may be utilized to facilitate the process. By way of example, FIG. 33 depicts one embodiment of a premature infant patient P fitted with a template for premature infants 450. By way of further example, FIG. 460 depicts one embodiment of a template for all other patients 460. As shown in FIG. 33, the patient P is a newborn patient. The patient P, however, may also be an adult or 16-year-old, for example. Each of the templates 450, 460 may be a thin, transparent, acrylic version of either the premature insert 410 with the surgical universal headrest 10 (FIG. 33) or the surgical universal headrest 10 in a closed position (FIG. 34).

Continuing to refer to FIG. 33, once the premature baby has been anesthetized and intubated while still supine in the transport warmer or on the OR table, the premature infant template 450 for prone positioning can be gently applied to the patient's face. Because the patient P is supine, the fitting process is relatively easy. The surgeon can look through the transparent template as well as through the central "window" created by the opening in the template 450 and see the patient's eyes. The surgeon then moves the template 450 cranially or caudally until the top of the template window is at least 2-3 mm above the supraorbital rims. The bi-maxillary support 416 with its maxillary gel pad 422 should then be loosened and moved cranially or caudally until the cranial surface of the maxillary gel pad 422 rests gently but snugly against both nares of the baby's nose. The knobs on each side of the bi-maxillary support 416 are then tightened. The premature infant template 450 is removed from the baby, and the surgeon takes the template over to the OR table where the surgical universal headrest 10 with its premature insert 410 has been set up. The surgeon sets the bi-maxillary support 416 of the premature insert 410 to be at the identical millimeter setting as that of the template 450. The baby can then be turned into the prone position with the nasal nares gently snugged up against the cranial side of the maxillary gel pad 422. To be safe, the surgeon again needs to check the baby's eyes visually—with a mirror at the very least—and then apply the multiple finger-tightened pins to achieve cranial stability.

Figure 34:
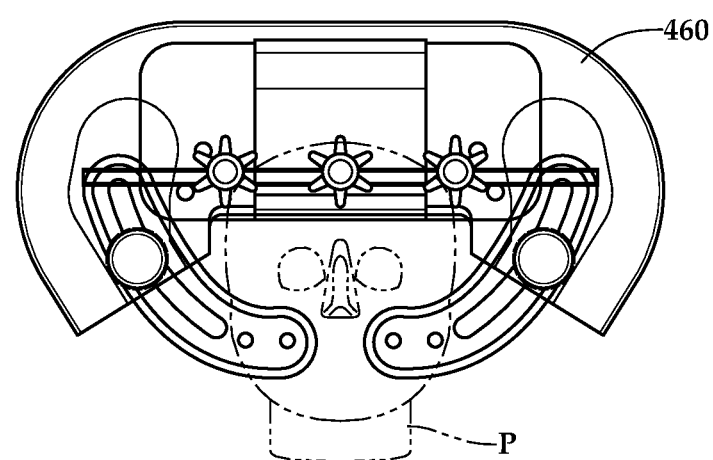
FIG. 34 is a ventral elevation view of one embodiment of a transparent acrylic template for prone surgery on all patients other than premature infants.

Referring now to FIG. 34, with respect to the template 460, once the patient has been anesthetized and intubated while still supine on a transport gurney or stretcher (for large patients) or the OR table (for babies and small children), the standard template can be gently applied to the patient's face. The "C" shaped template 460 mimics the geometry of the actual surgical universal headrest 10. When the template 460 is applied to the face, the curved lower arms form a "window" through which the surgeon can see the eyes of the patient. The template width should then be adjusted so that the lateral margins of the window approximate the lateral margins of the forehead.

The surgeon then positions the template 460 so that the top of the window is 3-4 mm above the supraorbital rims. The curved lower arms of the template 460 (which form the bottom of the window) are adjusted so that each of the distal ends of the lower arms is positioned just lateral to the patient's nostrils, and the superior margins of these rounded ends are no closer than 4-5 mm from the infraorbital rims. The lower arms are tightened in place with the knobs on the back of the template 460. The surgeon should recheck that the distal tips of the lower arms nave been positioned adjacent to the base of the nose and that these distal tips do not encroach on the eyes. Furthermore, it should be readily apparent that the lower arms are thereby positioned to provide support to the medial maxillae.

The surgeon can then move the template 460 over to the surgical universal headrest, which has already been attached to the OR table. The surgeon carefully superimposes the template onto the actual surgical universal headrest 10 and easily makes the appropriate adjustments so that the patient's face will safely and perfectly fit onto the headrest once the patient is carefully rolled into the prone position. Once the patient's head has been positioned appropriately, multiple low-pressure skull pins 150, 152, 154, 156, 158, 160, or more, should be applied to prevent movement.

Figure 35:
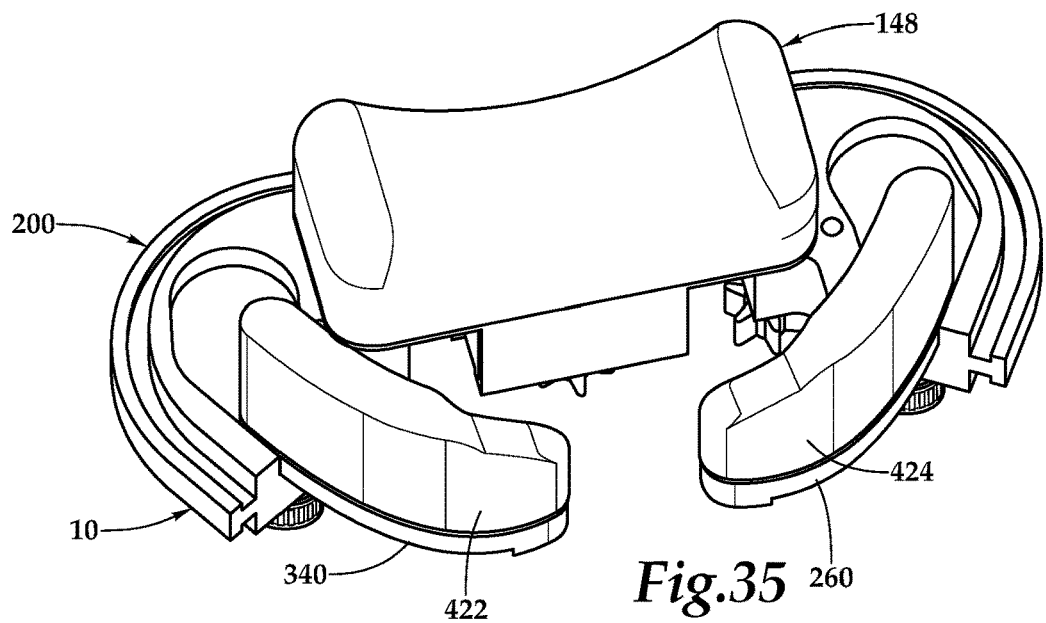
FIG. 35 is a caudal perspective view of the surgical universal headrest adjusted in size and fitted with a forehead gel pad and two maxillary gel pads to accommodate prone surgery on nearly all patients other than premature infants.
Figure 36:
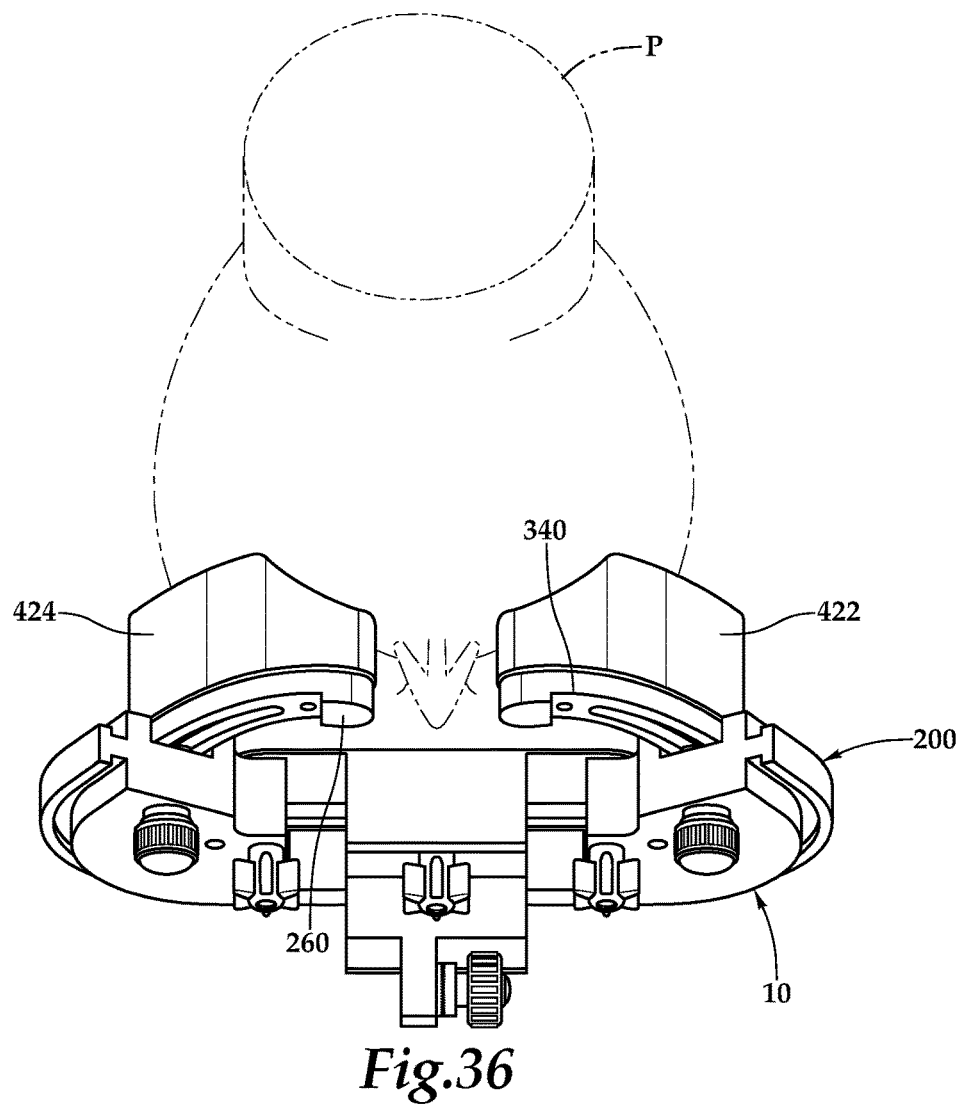
FIG. 36 is a ventral-caudal perspective view of a teen-age patient positioned prone on the surgical universal headrest depicted in FIG. 35.
Figure 37:
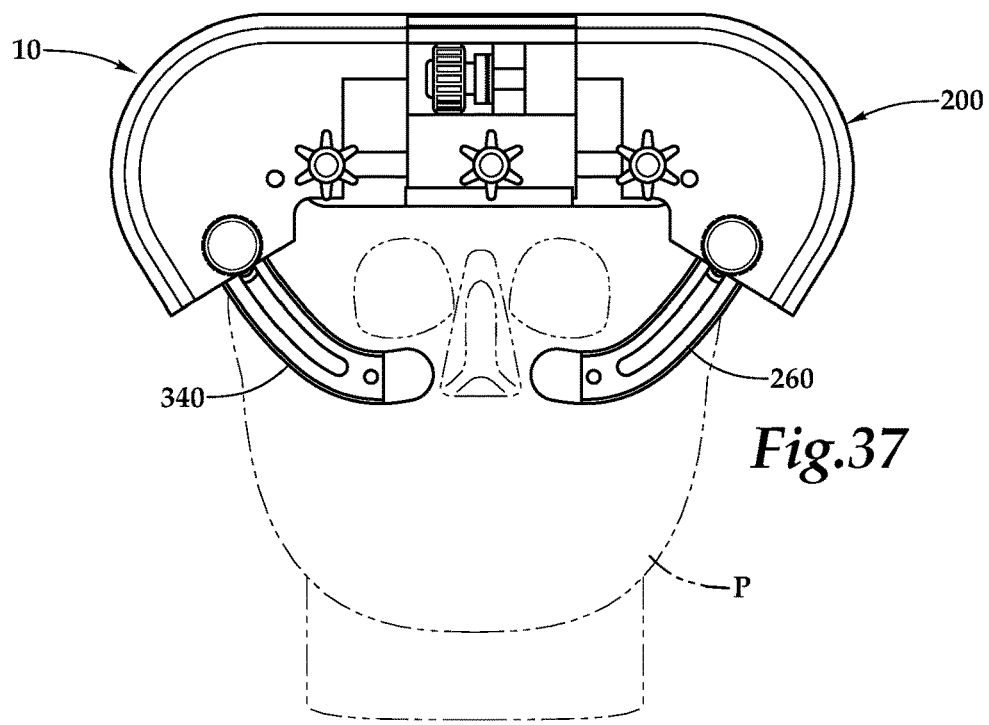
FIG. 37 is a ventral plan view of the teen-age patient prone on the surgical universal headrest depicted in FIG. 35, demonstrating no impingement of the eyes by the headrest.

Referring now to FIG. 35 through FIG. 47, various further configurations of the surgical universal headrest 10 with gel pad assemblies 148 for supporting the patient P are depicted to provide further examples. More particularly, FIG. 35 is a caudal perspective view of the surgical universal headrest 10 adjusted in size and fitted with a forehead gel pad 420 and two maxillary gel pads 422, 424 to accommodate prone surgery on nearly all patients other than premature infants. FIG. 36 is a ventral-caudal perspective view of a teen-age patient P positioned prone on the surgical universal headrest depicted in FIG. 35. Referring to FIG. 37, the teen-age patient P is prone on the surgical universal headrest 10 depicted in FIG. 35, demonstrating no encroachment of the eyes by the headrest.

Figure 38:
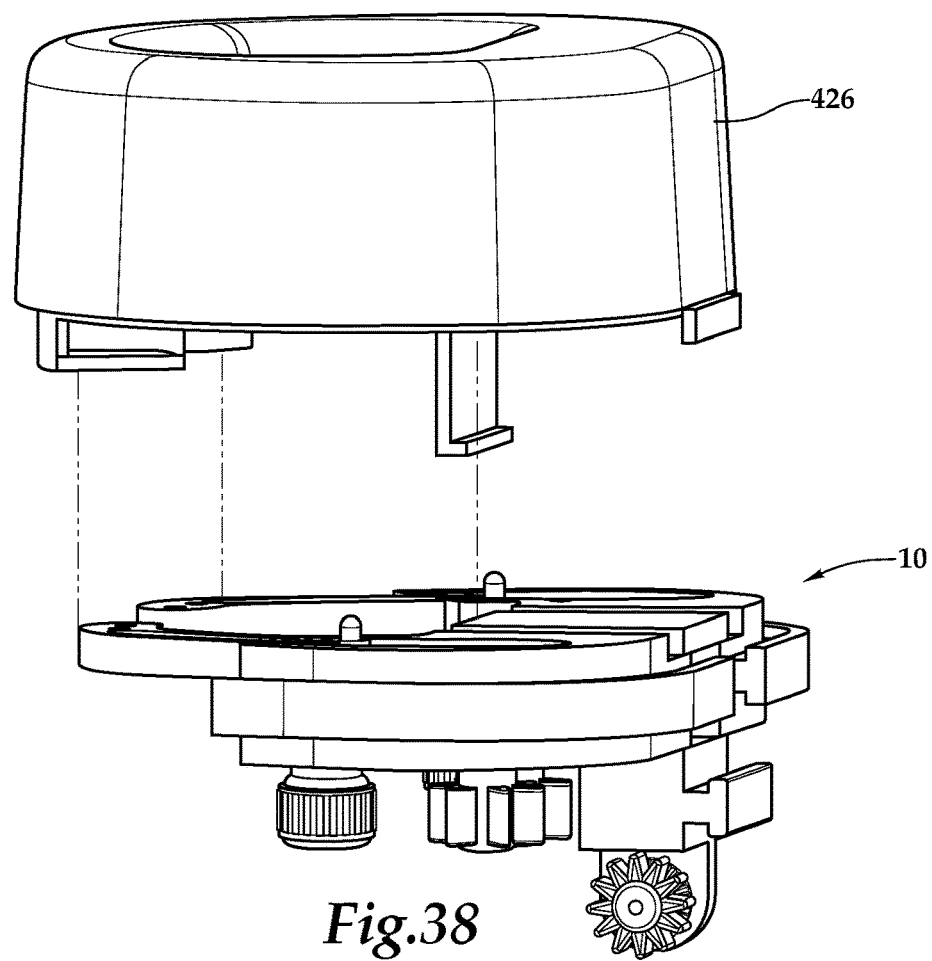
FIG. 38 is a lateral perspective view of the surgical universal headrest adjusted to accommodate a large patient in any position other than prone and fitted with an oval gel pad, dorsally displaced for clarity.
Figure 39:
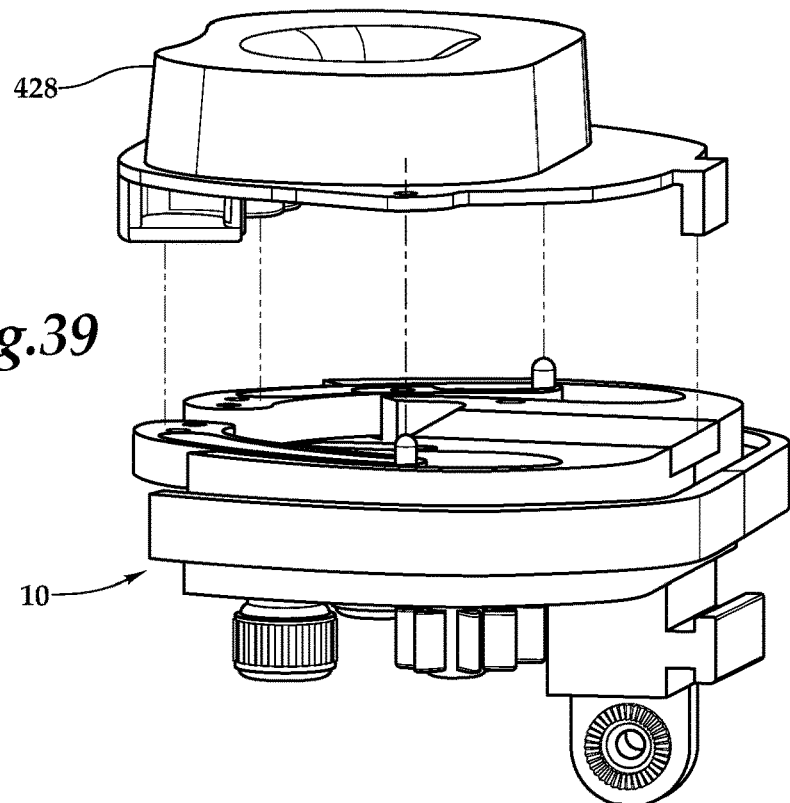
FIG. 39 is a lateral perspective view of the surgical universal headrest adjusted to accommodate a small baby in any position other than prone and fitted with an oval gel pad, dorsally displaced for clarity.
Figure 40:
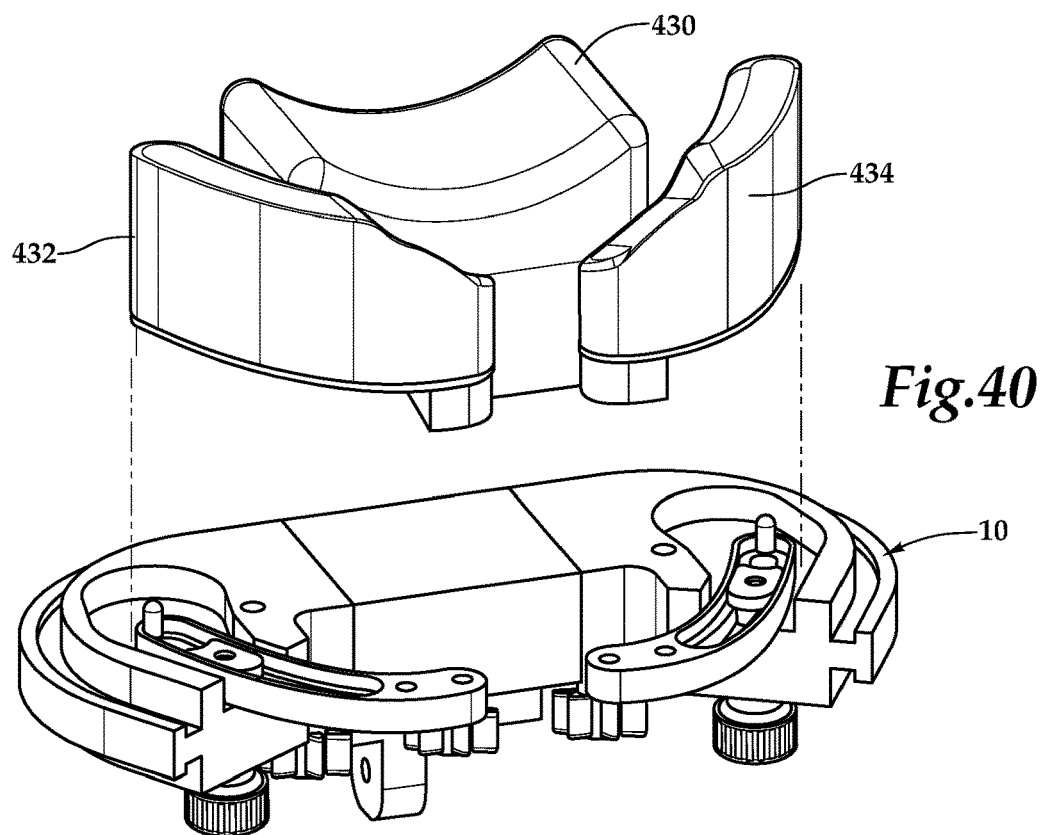
FIG. 40 is a caudal perspective view of the surgical universal headrest adjusted to have a closed condition to accommodate a small child or infant for prone surgery, requiring a frontal gel pad and two maxillary gel pads, dorsally displaced for clarity.
Figure 41:
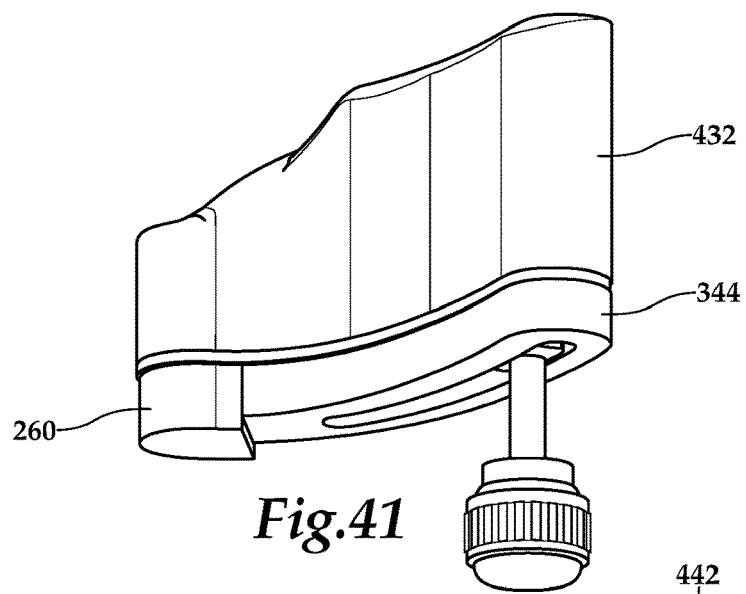
FIG. 41 is a medial cephalic perspective view of the right maxillary gel pad on the right arm depicted in FIG. 40 with the headrest removed for clarity, demonstrating the knob which positions and secures the glide within the elongated slot of an arm.
Figure 42:
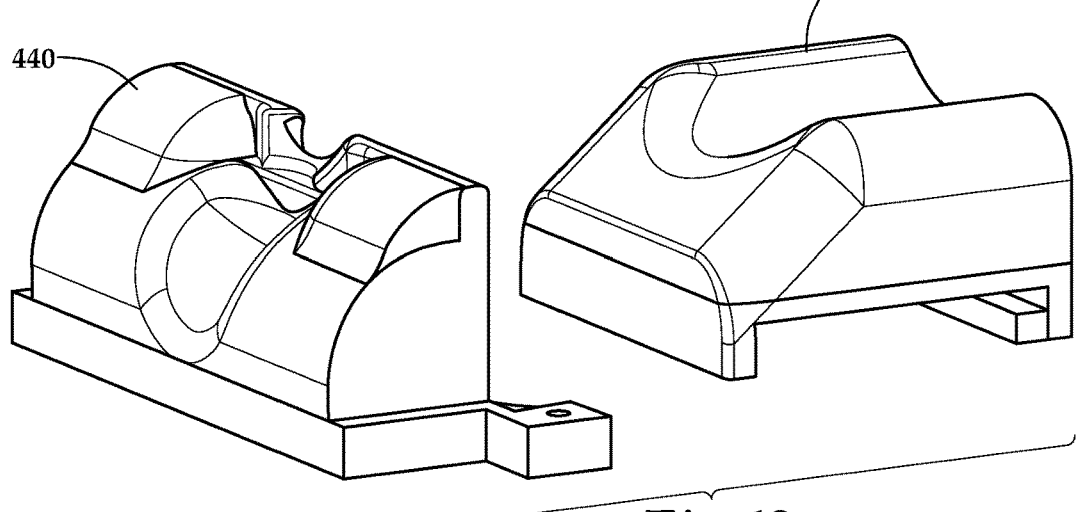
FIG. 42 is a cephalic-lateral perspective view of the maxillary and frontal gel pads utilized with the premature insert on the surgical universal headrest depicted in FIG. 44 for prone surgery on a premature infant.
Figure 45:
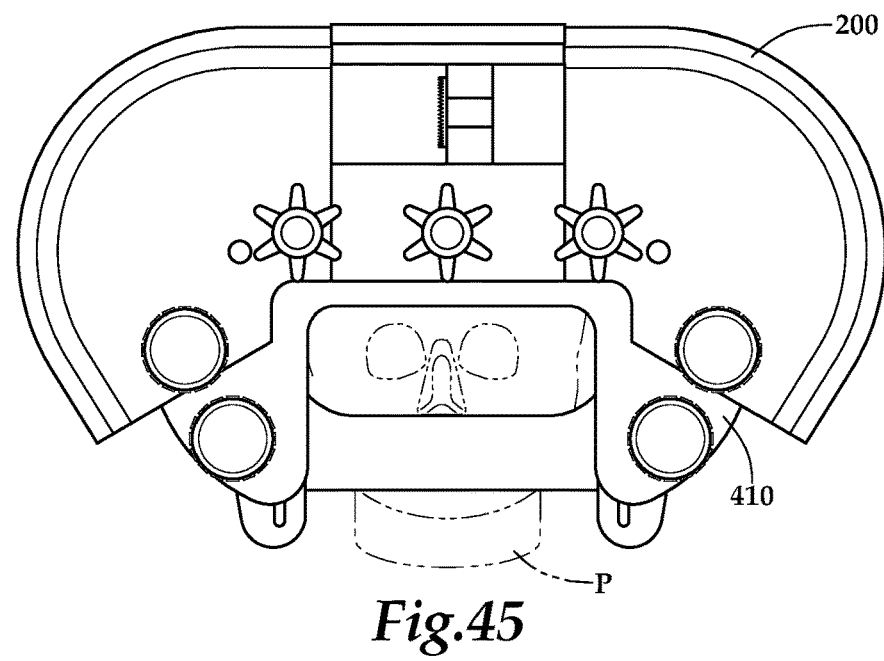
FIG. 45 is a ventral plan view of the surgical universal headrest with a premature insert in place and a premature infant positioned for prone surgery to demonstrate that the headrest does not impinge on the baby's eyes.

FIG. 38 is a lateral perspective view of the surgical universal headrest adjusted to accommodate a large patient P in any position other than prone and fitted with an oval gel pad 426, dorsally displaced for clarity. On the other hand, to show the range of capabilities, FIG. 39 is a lateral perspective view of the surgical universal headrest 10 adjusted to accommodate a small baby in any position other than prone and fitted with an oval gel pad 428, dorsally displaced for clarity. FIG. 40 is a caudal perspective view of the surgical universal headrest 10 adjusted to have a closed condition to accommodate a small child or infant patient P for prone surgery, requiring a frontal gel pad 430 and two maxillary gel pads 432, 434, dorsally displaced for clarity. FIG. 41 is a medial cephalic perspective view of the right maxillary gel pad 432 on the right arm depicted in FIG. 40 with the headrest removed for clarity, demonstrating the knob which positions and secures the glide within the elongated slot of an arm 344. Referring now to FIGS. 42 through 45, a cephalic-lateral perspective view of the maxillary and frontal gel pads 440, 442 utilized with the premature insert on the surgical universal headrest 10 are shown along with maxillary installation posts 418, 420. In particular, FIG. 45 is a ventral plan view of the surgical universal headrest 10 with a premature insert 410 in place and a premature infant positioned for prone surgery to demonstrate that the headrest does not impinge on the baby's eyes.

The order of execution or performance of the methods and process flows illustrated and described herein is not essential, unless otherwise specified. That is, elements of the methods and process flows may be performed in any order, unless otherwise specified, and that the methods may include more or less elements than those disclosed herein. For example, it is contemplated that executing or performing a particular element before, contemporaneously with, or after another element are all possible sequences of execution.

While this invention has been described with reference to illustrative embodiments, this description is not intended to be construed in a limiting sense. Various modifications and combinations of the illustrative embodiments as well as other embodiments of the invention, will be apparent to persons skilled in the art upon reference to the description. It is, therefore, intended that the appended claims encompass any such modifications or embodiments.

What is claimed is:

1. A skull pin holder assembly for use with a surgical headrest, comprising:
   a plurality of skull pin holders, each of the plurality of skull pin holders comprising:
      a pin having a tip and a base;
      a pin cup for holding the tip of the pin;
      a threaded barrel coupled to the base of the pin, the threaded barrel threadably engaging a locking block for adjusting the position of the pin;
      a mechanical pin pressure measuring device integrated into the threaded barrel, the mechanical pin pressure measuring device configured to measure the pressure exerted by the pin at the interface with the skull;
   a plurality of positioning arms mechanically supporting the plurality of skull pin holders with respect to rotation and height; and
   a plurality of locking levers for securing the plurality of positioning arms in place; and
   each of the plurality of skull pin holders being adjustably positioned on a rail, the rail configured to define at least a partial orbit around the skull for adjustable positioning of each pin holder along the rail.

2. The skull pin holder assembly as recited in claim 1, wherein the mechanical pin pressure measuring device further comprises a micro strain measuring device, the micro strain measuring device configured to electronically measure measuring resistance resulting from forces exerted at an interface of the pin and a skull, the micro strain measuring device outputting electronic data relative thereto.

3. The skull pin holder assembly as recited in claim 2, wherein the micro strain measuring device further comprises a strain gauge.

4. The skull pin holder assembly as recited in claim 2, wherein the micro strain measuring device further comprises strain gauge load cells.

5. The skull pin holder assembly as recited in claim 2, wherein the micro strain measuring device further comprises force sensors.

6. The skull pin holder assembly as recited in claim 1, further comprising a transmitter communicatively coupled to the mechanical pin pressure measuring device, the transmitter wirelessly transmitting the electronic data.

7. The skull pin holder assembly as recited in claim 6, wherein the transmitter utilizes a wireless methodologies selected from the group consisting of 802.11, 3G, 4G, Edge, WiFi, ZigBee, near field communications (NFC), and Bluetooth.

8. The skull pin holder assembly as recited in claim 6, wherein the transmitter utilizes a Bluetooth wireless communication standard.

9. The skull pin holder assembly as recited in claim 1, wherein the rail forms a portion of a surgical universal headrest.

10. The skull pin holder assembly as recited in claim 1, wherein the rail forms a portion of a surgical universal headrest, the surgical universal headrest defining a support permitter of adjustable size having an opening therethrough.

* * * * *